(12) United States Patent
Kurata et al.

(10) Patent No.: US 9,597,681 B2
(45) Date of Patent: Mar. 21, 2017

(54) SENSOR ELEMENT, METHOD FOR MANUFACTURING SENSOR ELEMENT, AND SENSOR CARTRIDGE

(71) Applicant: ARKRAY, Inc., Kyoto (JP)

(72) Inventors: Yuji Kurata, Kyoto (JP); Hisashi Kaneda, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 14/710,486

(22) Filed: May 12, 2015

(65) Prior Publication Data

US 2015/0328632 A1 Nov. 19, 2015

(30) Foreign Application Priority Data

May 13, 2014 (JP) .................. 2014-099807
Apr. 7, 2015 (JP) .................. 2015-078424

(51) Int. Cl.
*G01N 21/00* (2006.01)
*B01L 3/00* (2006.01)
(Continued)

(52) U.S. Cl.
CPC ............ *B01L 3/50* (2013.01); *B32B 37/22* (2013.01); *B32B 38/0004* (2013.01); *C12Q 1/54* (2013.01);
(Continued)

(58) Field of Classification Search
CPC ....... G01N 33/48764; G01N 35/00009; G01N 2035/00019; G01N 2021/478; G01N 2201/0415; G01N 2201/0621; A61B 5/14532; A61B 2562/0295; A61B 19/02; A61B 2017/00265; A61B 5/15169; A61B 5/15176; A61B 5/157; B01L 3/545; B01L 2300/0819; B01L 2300/0887; B01L 2300/161; B01L 2300/16; B01L 2300/0663;
(Continued)

(56) References Cited

U.S. PATENT DOCUMENTS

2005/0221470 A1* 10/2005 Matsumoto ............... B01L 9/52
435/287.1
2008/0129280 A1 6/2008 Kaimori et al.
(Continued)

FOREIGN PATENT DOCUMENTS

JP 2011-508872 A 3/2011
JP 5289666 B2 9/2013
WO 2013/038691 A1 3/2013

OTHER PUBLICATIONS

The partial European search report (R. 64 EPC) issued by the European Patent Office on Oct. 14, 2015, which corresponds to European Patent Application No. 15167667.3-1559 and is related to U.S. Appl. No. 14/710,486.
(Continued)

*Primary Examiner* — Dennis M White
(74) *Attorney, Agent, or Firm* — Studebaker & Brackett PC

(57) ABSTRACT

A sensor element comprising a tape-shaped mount film; and a plurality of film-shaped sensors bonded on one surface of the mount film, wherein the front and rear film-shaped sensors are spaced at a predetermined distance in a lengthwise direction of the mount film, and a crosswise length of each film-shaped sensor is shorter by a predetermined quantity than a crosswise length of the mount film.

9 Claims, 22 Drawing Sheets

(51) Int. Cl.
  *C12Q 1/54* (2006.01)
  *B32B 38/00* (2006.01)
  *B32B 37/22* (2006.01)
  *G01N 33/487* (2006.01)

(52) U.S. Cl.
  CPC .... *G01N 33/48764* (2013.01); *B01L 2200/10* (2013.01); *B01L 2200/12* (2013.01); *B01L 2300/0609* (2013.01); *B01L 2300/0663* (2013.01); *B01L 2300/0803* (2013.01); *B01L 2300/0819* (2013.01); *B01L 2300/0887* (2013.01); *B01L 2300/16* (2013.01); *B01L 2300/161* (2013.01); *B32B 2535/00* (2013.01); *Y10T 156/1082* (2015.01)

(58) Field of Classification Search
  CPC ......... B01L 2200/10; B01L 2300/0609; B01L 2200/12; B01L 2300/0803; B01L 3/50; B32B 2535/00; B32B 38/0004; B32B 37/22; C12Q 1/54; Y10T 156/1082
  See application file for complete search history.

(56) References Cited

U.S. PATENT DOCUMENTS

| | | |
|---|---|---|
| 2009/0149725 A1 | 6/2009 | Gofman et al. |
| 2009/0263854 A1 | 10/2009 | Jacono et al. |
| 2012/0094369 A1 | 4/2012 | Jackson et al. |
| 2012/0282138 A1 | 11/2012 | Gofman et al. |
| 2014/0135606 A1* | 5/2014 | Yasui ................ A61B 5/14532 600/365 |

OTHER PUBLICATIONS

The extended European search report issued by the European Patent Office on Feb. 1, 2016, which corresponds to European Patent Application No. 15167667.3-1559 and is related to U.S. Appl. No. 14/710,486.

Communication pursuant to Article 94(3) EPC issued by the European Patent Office on Jan. 23, 2017, which corresponds to European Patent Application No. 15167667.3-1559 and is related to U.S. Appl. No. 14/710,486.

* cited by examiner

SENSOR ELEMENT, METHOD FOR MANUFACTURING SENSOR ELEMENT, AND SENSOR CARTRIDGE

CROSS-REFERENCE TO RELATED APPLICATION

This application is based upon and claims the benefit of priority of the prior Japanese Patent Applications No. 2014-099807 filed on May 13, 2014 and No. 2015-078424 filed on Apr. 7, 2015, the entire contents of which are incorporated herein by reference.

TECHNICAL FIELD

The present invention relates to a sensor element, a method for manufacturing a sensor element, and a sensor cartridge.

BACKGROUND ART

An apparatus used by setting a cartridge incorporating a seal tape to which a plurality of sensors for testing is stuck, is known as an apparatus for measuring a blood component instanced by a blood glucose level and other equivalent blood components by use of a sensor (e.g., Patent Document 1). Known also is a sensor chip connected element configured to cut and segment respective sensor chips at high efficiency (Patent Document 2).

It is, however, a status quo that a sensor element being easy to take out a sensor and to be manufactured is not yet developed.

DOCUMENTS OF PRIOR ARTS

Patent Documents

[Patent Document 1] Japanese Patent Application Laid-Open Publication No. 2011-508872
[Patent Document 2] Japanese Patent Application Publication No. 5289666

SUMMARY

It is a first object of the present invention, which was devised in view of the foregoing status quo, to provide a sensor element being easy to take out a sensor and to be manufactured.

It is a second object of the present invention to provide a method for manufacturing a sensor element sensor element that is easy to take out a sensor and can be easily manufactured.

It is a third object of the present invention to provide a sensor cartridge that is easy to take out a sensor and can be manufactured at a low cost.

For accomplishing the first object, a sensor element according to the present invention is configured to include: a tape-shaped mount film; and a plurality of film-shaped sensors bonded on one surface of the mount film, wherein the front and rear film-shaped sensors are spaced at a predetermined distance in a lengthwise direction of the mount film, and a crosswise length of each film-shaped sensor is shorter by a predetermined quantity than a crosswise length of the mount film.

To be specific, the plurality of film-shaped sensors is bonded to the mount film for the sensor element so that the two adjacent film-shaped sensors are spaced at a predetermined distance. The take-out of the film-shaped sensor from the sensor element according to the present invention is easier than a sensor element with the plurality of film-shaped sensors being bonded onto the mount film without any space.

The crosswise length of each film-shaped sensor of the sensor element according to the present invention is shorter by a predetermined quantity than a crosswise length of the mount film. Accordingly, the manufacture of the sensor element according to the present invention entails building up a structure of bonding a stacked body including the plurality of film-shaped sensors and the mount film together by use of a bonding layer (composed of a bonding/adhesive material instanced by a double-sided tape and other equivalent layers), in which such a state occurs that the portions other than the film-shaped sensors of the stacked body in the structure are connected when half-cutting a boundary portion of each film-shaped sensor of the stacked body in the structure up to the bonding layer from the side of the stacked body. On the other hand, when half-cutting the structure related to the sensor element in which the crosswise length of each film-shaped sensor is equal to the crosswise length of the mount film, this results in occurrence of a state of coexistence of the plurality of film-shaped sensors and film-shaped portions not including the plurality of film-shaped sensors on the mount film.

With the film-shaped portions not including the plurality of film-shaped sensors remaining on the mount film, the film-shaped portion is also taken out as the case may be when taking out the film-shaped sensor from the mount film. It is therefore necessary to remove each film-shaped portion on the mount film, however, when the portions remaining on the mount film but not including the film-shaped sensors are connected, the film-shaped sensor can be taken out from the mount film, with these portions not becoming obstacles, without removing these portions from the mount film. It can be therefore said that the sensor element according to the present invention is easier to be manufactured to such a degree as not to remove the portions of the stacked body other than the film-shaped sensors after being half-cut than "the sensor element required to remove the film-shaped portions after being half-cut". The step of removing the connected portions is conducted easier than the step of removing the plurality of film-shaped portions. Hence, it can be said that the sensor element not including the portions other than the film-shaped sensors according to the present invention is also easier to be manufactured than "the sensor element required to remove the film-shaped portions after being half-cut".

The sensor element according to the present invention may be configured so that an end portion of the film-shaped sensor is exfoliated from the mount film when bending a portion, under the end portion of a certain film-shaped sensor, of the mount film in a longitudinal direction of the sensor element at a curvature equal to or smaller than a predetermined curvature with a posture of directing inward an undersurface defined as a surface different from the one surface. In other words, the sensor element according to the present invention may be configured so that a part of the film-shaped sensor is exfoliated from the mount film upon bending in a predetermined direction. When apart of the film-shaped sensor is exfoliated from the mount film, the film-shaped sensor can be taken out from the sensor element with a simple mechanism by making use of the exfoliated portion. It therefore follows that when the sensor element according to the present invention is configured to exfoliate a part of the film-shaped sensor from the mount film, a configuration of a measurement apparatus using the sensor element can be simplified.

On the occasion of attaining (manufacturing) the sensor element according to the present invention, a hygroscopic property may be given to the mount film so that deterioration of the film-shaped sensor due to a water content (humidity) can be inhibited.

The sensor element according to the present invention may adopt a configuration that "each film-shaped sensor include recessed portions or protruded portions provided at two face-to-face end portions thereof, and each film-shaped sensor is configured so that the end portions provided with the recessed portions or the protruded portions are bonded substantially in parallel to a longitudinal direction of the mount film at a central portion of the one surface of the mount film. Note that when adopting the configuration described above, it follows that the recessed portions or the protruded portions existing in or on the film-shaped sensors can be used for taking out the film-shaped sensors from the sensor element. Accordingly, the foregoing configuration being adopted, it is feasible to acquire the sensor element that is easier to take out the film-shaped sensor in the measurement apparatus.

A method for manufacturing a sensor element, includes: a step of forming a sensor element by bonding a continuous stacked body including a plurality of film-shaped sensors with a bonding layer being interposed between the film-shaped sensor and the sensor element; and a step of half-cutting a boundary portion of each film-shaped sensor of the sensor element up to at least the bonding layer from the side of the stacked body. When the boundary portion of each film-shaped sensor is half-cut up to the bonding layer, the film-shaped sensor can be easily exfoliated from the mount film by bending the sensor element. The method of manufacturing the sensor element according to the present invention can be therefore said to be a method enabling the manufacture of the sensor element facilitating the exfoliation of each film-shaped sensor from the mount film. Note that the sensor element manufactured by the sensor element manufacturing method according to the present invention may be configured so that the portions, not including the film-shaped sensors, of the stacked body remain on the mount film and may also be configured so that these portions do not remain on the mount film. "The half-cutting step" may be a step of "half-cutting the mount film from the side of the stacked body at the boundary portion of each film-shaped sensor of the sensor element".

To accomplish the third object described above, a sensor cartridge according to the present invention "includes: a reel to be wound with the sensor element according to any one of claims 1 through 3; a case to house the reel therein, the case including a sensor protruding port to admit passage of the sensor element wound on the reel and a film housing port to admit passage of the mount film for the sensor element, the sensor protruding port receiving insertion of the sensor element unwound from the reel with a posture of directing an undersurface of the mount film toward the film housing port; and a rotary body to be housed in the case and enabled to rotate from outside the case, the rotary body driving the sensor element in an unwinding direction of the sensor element wound on the reel, the sensor element being inserted into the sensor protruding portion with the posture of directing the undersurface of the mount film toward the film housing port and returning to within the case via the film housing port after the film-shaped sensor has been removed at a portion in the vicinity of the sensor protruding port, wherein a portion of the case, existing between the sensor protruding port and the film housing port, has such a shape that at least a part of the mount film is bent at a curvature equal to or smaller than the predetermined curvature when bending the mount film along the portion of the case".

Namely, the sensor cartridge according to the present invention includes the sensor element according to the present invention. The sensor element according to the present invention is easily manufactured as described above. It therefore follows that the sensor cartridge according to the present invention can be manufactured at a low cost to a degree of easiness of manufacturing the sensor element (a degree of lessening the number of steps necessary for manufacturing the sensor element). The sensor cartridge according to the present invention has a configuration that when rotating the rotary body, the end portion of the film-shaped sensor is exfoliated from the mount film and protrudes from the case (the sensor protruding port of the case). When a part of the film-shaped sensor protrudes from the case, the film-shaped sensor can betaken out from the sensor element with the simple mechanism by making use of the protruded portion. It can be therefore said that the sensor cartridge according to the present invention is configured to take out the sensor in the measurement apparatus having the simple configuration.

On the occasion of attaining the sensor cartridge according to the present invention, it is preferable that "the sensor element is wound on the reel with the sensor element with a posture of directing inward the one surface of the mount film" in order to inhibit the film-shaped sensor at the outermost peripheral portion of the sensor element wound on the reel from being exfoliated from the mount film.

According to the present invention, it is feasible to provide the sensor element being easy to take out the sensor and to be manufactured, the sensor element manufacturing method capable of easily manufacturing the sensor element being easy to take out the sensor, and the sensor cartridge that is easy to take out the sensor and can be manufactured at the low cost.

DESCRIPTION OF EMBODIMENTS

<<First Embodiment>>

Figure 1:
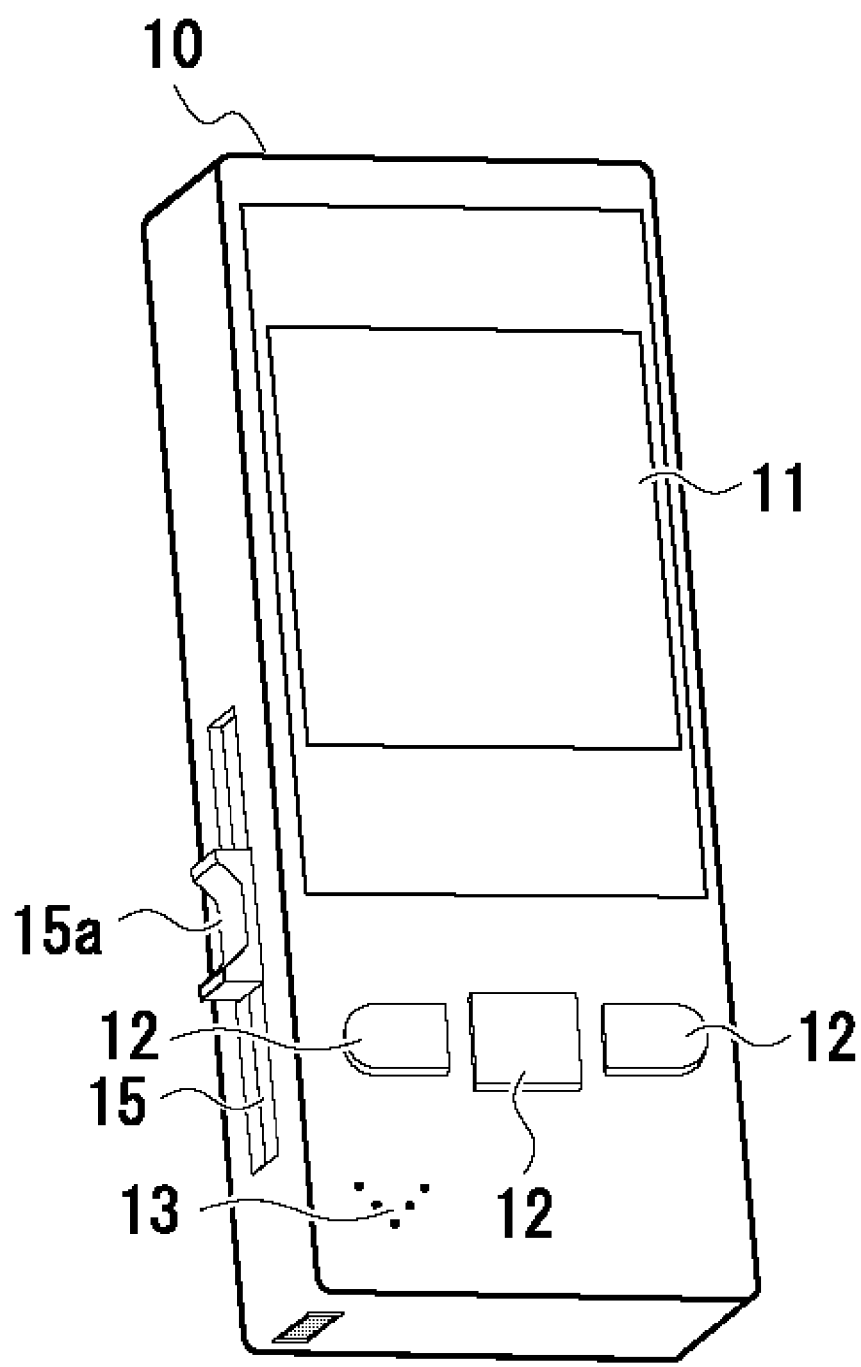
FIG. 1 is a diagram of an external appearance of a measurement apparatus according to a first embodiment of the present invention.

FIG. 1 illustrates an external appearance of a measurement apparatus according to a first embodiment of the present invention.

The measurement apparatus according to the first embodiment is a blood glucose level measurement apparatus that is used by setting a sensor cartridge therein. As illustrated in FIG. 1, the measurement apparatus includes an apparatus enclosure 10, an LCD (Liquid Crystal Display) 11, three push button switches 12 and a speaker 13, these components 11, 12, 13 being disposed on a front surface (the surface on the near side in FIG. 1) of the apparatus enclosure 10. The measurement apparatus further includes slider 15 sliding vertically together with a slider knob 15a by operating the slider knob 15a disposed on a side surface of the apparatus enclosure 10.

Figure 3:
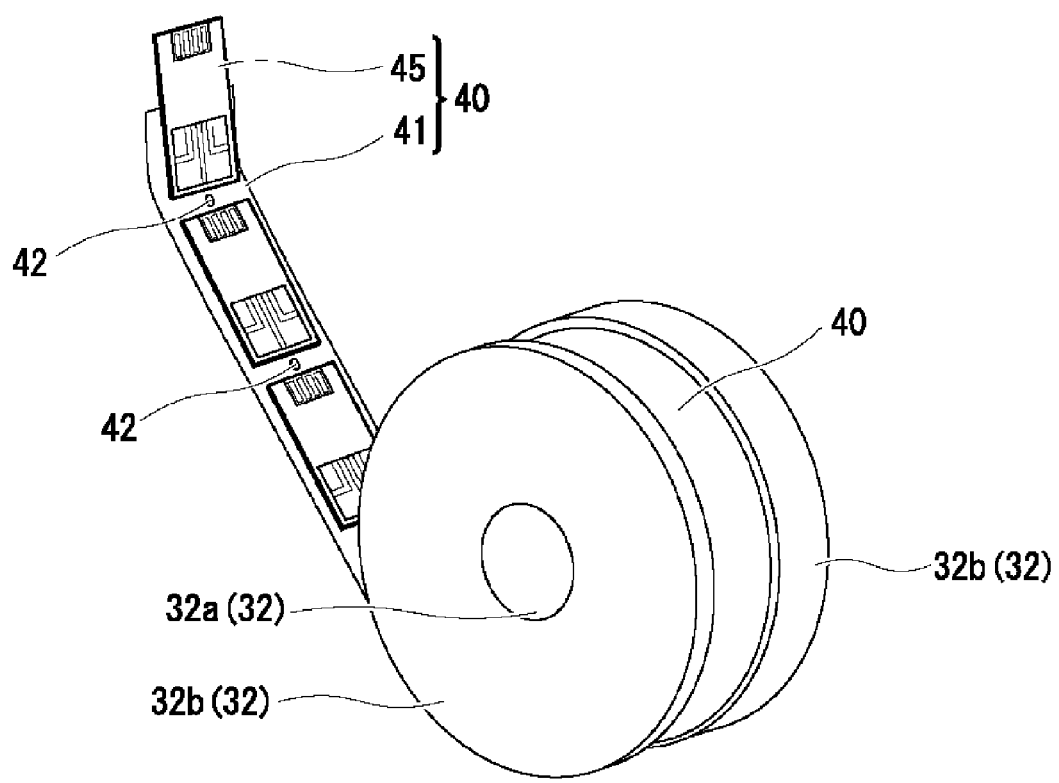
FIG. 3 is a view of an external appearance of a reel hub wound with a sensor element, the hub being housed in the sensor cartridge.
Figure 4A:
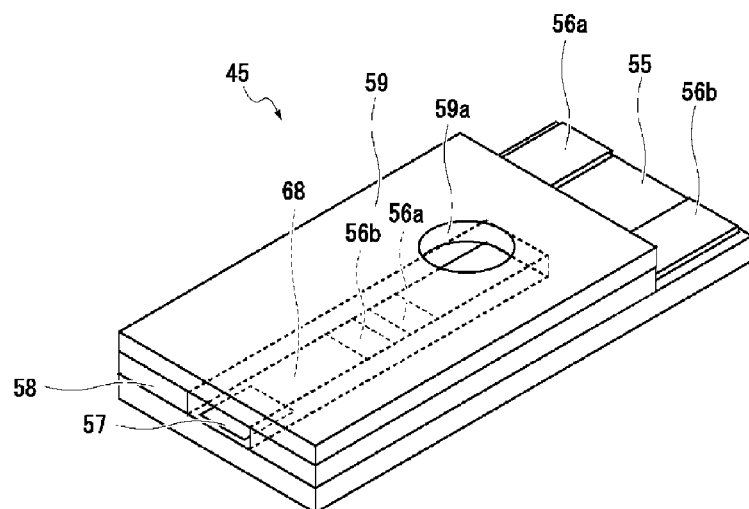
FIG. 4A is an explanatory view of an example of a configuration of a film-shaped sensor.
Figure 4B:
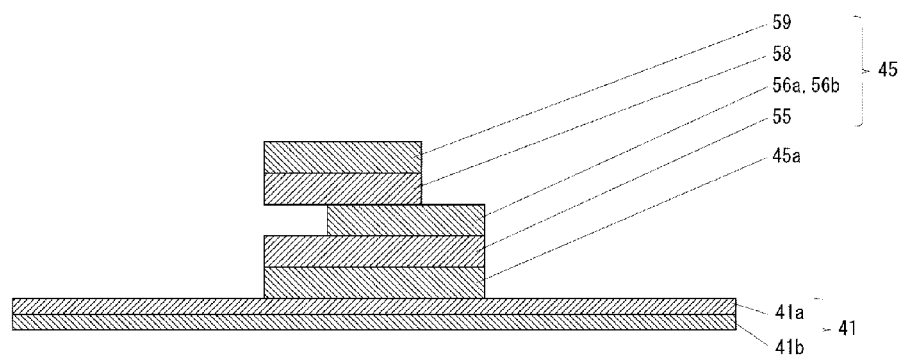
FIG. 4B is a sectional view illustrating an example of a configuration of the sensor element.
Figure 4C:
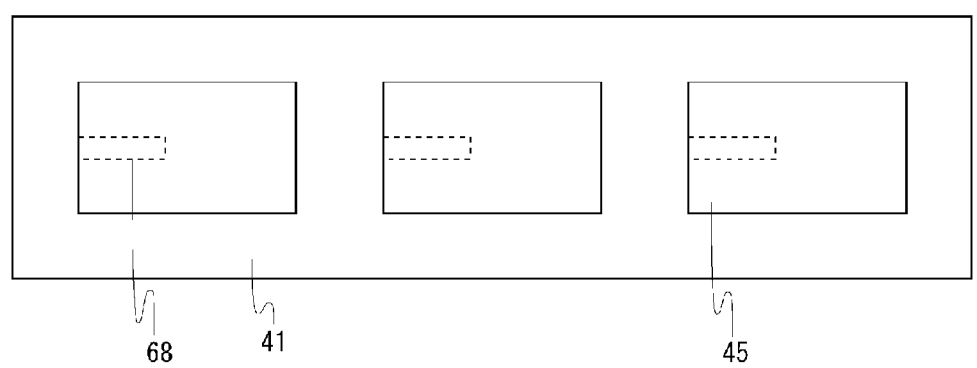
FIG. 4C is a top view of the example of the configuration of the sensor element.
Figure 5:
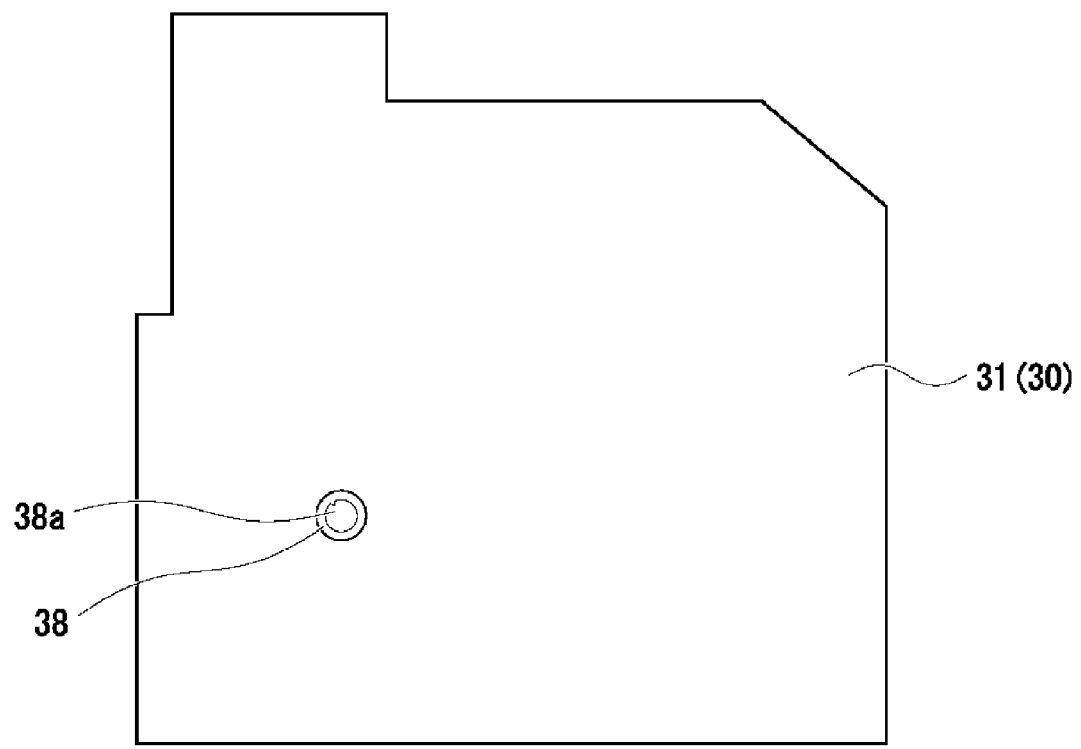
FIG. 5 is a view of an external appearance of a sensor cartridge.

To begin with, a configuration of a sensor cartridge 30 to be set in the measurement apparatus will be described with reference to FIGS. 2-5. Note that FIG. 2 in these drawings is a principal sectional view of principal portions of the measurement apparatus with the sensor cartridge 30 being set therein, the view being taken along a plane (passing through substantially a center of the slider knob 15a) orthogonal to a thicknesswise direction. FIG. 3 is a view of an external appearance of a reel hub 32 wound with a sensor element 40, the hub being housed in the sensor cartridge 30. FIG. 4A is an explanatory view illustrating an example of a configuration of a film-shaped sensor 45. FIG. 4B is a sectional view illustrating an example of a configuration of the sensor element 40. FIG. 4C is a top view of the sensor element 40. FIG. 5 is a view of an external appearance of the sensor cartridge 30 as viewed from the same side as in FIG. 2.

Figure 2:
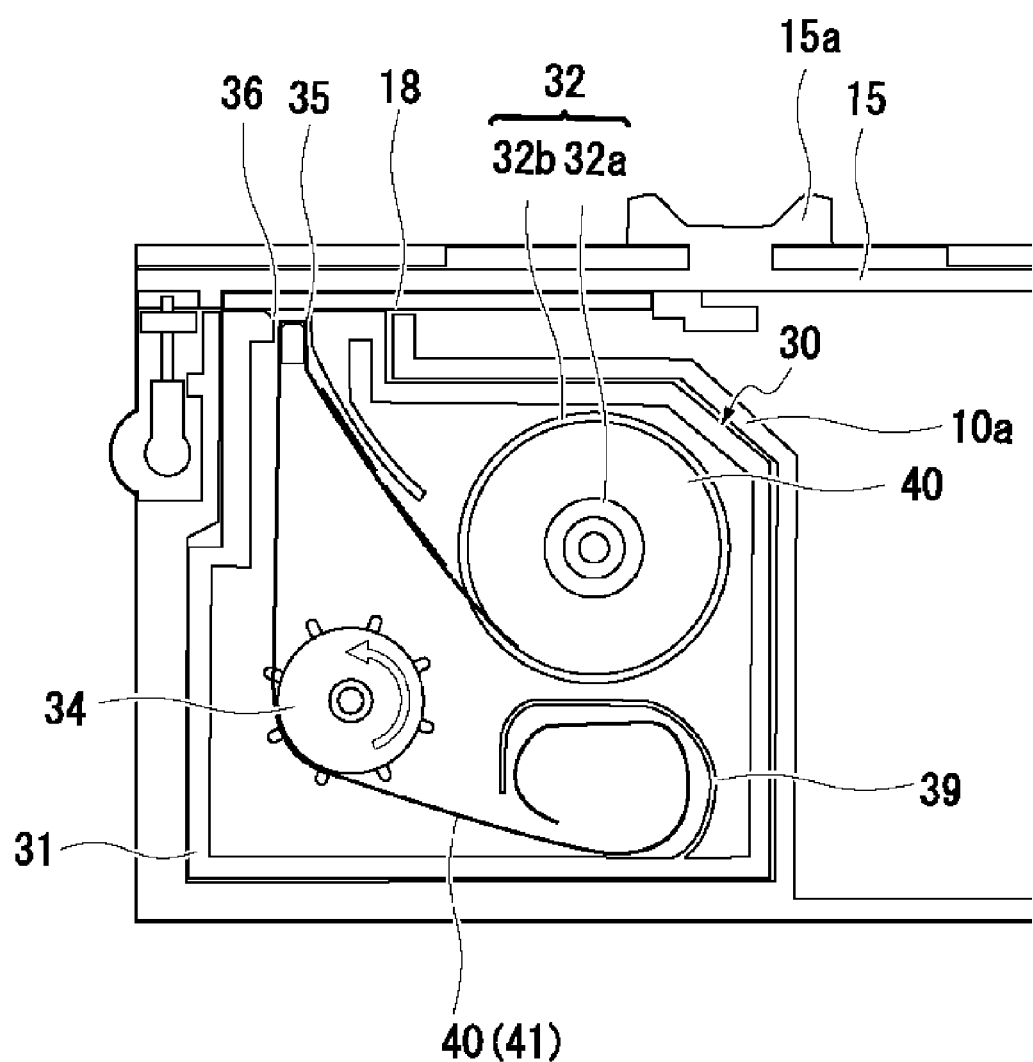
FIG. 2 is a a principal sectional view of principal portions of the measurement apparatus according to the first embodiment, with a sensor cartridge being set therein, the view being taken along a plane orthogonal to a thicknesswise direction.

As apparent from the sectional view depicted in FIG. 2, the sensor cartridge 30 is configured by housing the reel hub 32 wound with the sensor element 40 in a case 31. The enclosure 10 of the measurement apparatus includes a cartridge housing unit 10a provided for housing the sensor cartridge 30.

The sensor element 40 (FIG. 3) is a tape-shaped member including a plurality of small-sized film-shaped sensors 45 bonded to amount film 41 by using a bonding material having a substantially weak bonding strength, the sensors 45 being at an equal interval in a lengthwise direction of the film 41. Holes 42 each taking a rectangular shape with rounded corners are formed at the same interval as the interval (an interval between centers of the two neighboring film-shaped sensors 45, which will hereinafter be referred to as a sensor disposing interval) of disposing the film-shaped sensors 45 in portions with the film-shaped sensors 45 not being disposed.

It may be sufficient that the mount film 41 of the sensor element 40 is a film being is flexible but substantially hard to extend. Hence, the mount film 41 may involve using a resinous film, a laminated body of two or more types of resinous films, a laminated body of the resinous film and a metallic film, a body configured by embedding a metal wire or other equivalent material into the resinous film. However, the mount film 41 may have a hygroscopic property in order to restrain the film-shaped sensor 45 from deteriorating due to moisture. It is preferable in this case that the mount film 41 is formed of a material (the laminated body of the hygroscopic film and another film, and other equivalent materials) containing a hygroscopic substance.

Each of the film-shaped sensors 45 disposed on the mount film 41 is a sensor having, e.g., a configuration as schematically illustrated in FIG. 4A. To be specific, the film-shaped sensor 45 is, e.g., a sensor including: a substrate formed with an enzyme membrane 57 to retain an enzyme reacting with a glucose, an electron acceptor and other equivalent chemical entities and with a plurality of electrodes 56a, 56b for detecting an oxidation reduction potential or an oxidation reduction current; a cover 59 stacked on the substrate 55, the cover being provided with a through-hole 59a via U-shaped spacer 58; and a flow path 68 for supplying a blood spotted on a front end portion thereof to the enzyme membrane, the flow path 68 being defined by the substrate 55, the spacer 58 and the cover 59.

The sensor element 40 housed in the sensor cartridge 30 involves using a material enabling the film-shaped sensor 45 to be exfoliated from the mount film 41 when folded from a disposing surface of the film-shaped sensor 45 to be convexed. More specifically, the sensor element 40 involves using such a material that a bending stress exceeding the bonding strength to the mount film 41 occurs at the end portion of the film-shaped sensor 45 disposed on the bent portion when bending a portion with a certain film-shaped sensor 45 being disposed thereon at a curvature equal to or smaller than a predetermined curvature so that the disposing surface of the film-shaped sensor 45 is convexed.

The sensor element 40 meeting the specifications described above can be manufactured by adopting a configuration illustrated in, e.g., FIGS. 4B and 4C. In other words, the film-shaped sensor 45 involves using a laminated body configured by laminating a double-sided sheet tape serving as the spacer 58 and a hydrophilic film serving as the cover 59 on a PET (polyethylene terephthalate) sheet serving as the substrate 55 formed with the electrodes and other equivalent components. The mount film 41 involves using a laminated body configured by a base sheet (e.g., the PET sheet) 41a on a desiccant sheet (hygroscopic sheet) 41b, and an adhesive sheet (e.g., Easy peel sheet) 45a is used for bonding the film-shaped sensor 45 and the mount film 41 together.

The sensor element 40 having the configuration illustrated in FIGS. 4B and 4C can be manufactured by forming the laminated body with the film existing between the film-shaped sensors 45, and thereafter forming the hole 42 after half cutting and thus removing an unnecessary portion (between the film-shaped sensors 45) positioned more upward than the adhesive sheet up to a halfway point of the adhesive sheet (alternatively half cutting and thus removing the unnecessary portion positioned more upward than the adhesive sheet up to the halfway point of the adhesive sheet after forming the hole 42). Note that the half-cut can be attained by a pinnacle cutter, a Thomson cutter, a mold or a laser cutter and other equivalent cutters.

The sensor element 40 according to the first embodiment is, as apparent from FIG. 3, configured so that a width of each film-shaped sensor 45 is narrower than a width of the mount film 41, and each film-shaped sensor 45 is disposed at the central portion of the mount film 41 in a widthwise direction. The sensor element 40 can be therefore manufactured by half cutting and thus removing the unnecessary portions batchwise.

The reel hub 32 (FIGS. 2 and 3) wound with the sensor element 40 is a member configured by connecting two doughnut-shaped flanges 32b with a cylindrical portion 32a while inserting the cylindrical portion 32a through apertures formed in the central portions of the flanges 32b at an interval slightly wider than the width of the sensor element 40.

The reel hub 32 is housed in the case 31 in a state of being wound with the sensor element 40 when assembling the cartridge 30. Concretely, the case 31 is provided with a reel hub securing shaft extending in a thicknesswise direction (vertical to a sheet surface of FIG. 2) of the case 31 and having an outside diameter slightly smaller than an inside diameter of the cylindrical portion 32a of the reel hub 32. The reel hub 32 is housed in the case 31 in a way of inserting the reel hub securing shaft into the cylindrical portion 32a after winding the sensor element 40 along a periphery of the cylindrical portion 32a when assembling the cartridge 30.

Note that when winding the sensor element 40 on the reel hub 32 in a way of directing outward the surface provided with the film-shaped sensor 45, such a possibility occurs that the film-shaped sensor 45 existing at an outermost peripheral portion of the sensor element 40 wound on the reel hub 32 is exfoliated due to vibrations or other equivalent phenomena of the measurement apparatus. It is therefore preferable that the reel hub 32 is, as illustrated in FIG. 3, wound with the sensor element 40 in the way of directing inward the surface provided with the film-shaped sensor 45. FIG. 3 illustrates the sensor element 40 provided with the film-shaped sensors 45 up to a leading end of the mount film 41. However, the sensor element 40 wound on the reel hub 32 incorporated into the cartridge 30 is configured not to dispose the film-shaped sensor 45 at a portion (termed hereinafter a lead portion) having a predetermined length on the side of the leading end but to form the holes 42 at the disposing interval of the sensors.

A plurality of protrusions is provided along the reel hub securing shaft of the case 31 (FIG. 2), the protrusions engaging with the protrusions provided on the flange 32b on the side opposite to the case 31 to restrain the reel hub 32 from rotating in a winding direction of the sensor element 40.

The case 31 is provided with a roller securing shaft extending in a thicknesswise direction of the case 31. The case 31 houses a roller 34 enabled to rotate about the roller securing shaft, the roller 34 taking a cylindrical shape and including a plurality of pins disposed at an equal interval along an external surface thereof.

The pins of the roller 34 are inserted into the foregoing holes 42 (FIG. 3) of the sensor element 40. A diameter of the roller 34, a number of the pins disposed along the external surface of the roller 34 and the sensor disposing interval are determined so as to insert the pins into the holes 42 of the sensor element 40.

A fitting portion 38 taking a shape as illustrated in FIG. 5 is provided on the near side in FIG. 2 as viewed from the roller 34, the fitting portion 38 being configured to rotate together with the roller 34.

To be specific, the fitting portion 38 is provided on the near side of the roller 34, the fitting portion 38 being formed with a circular recessed portion 38a including a portion protruding toward the central side. The case 31 of the sensor cartridge 30 includes an aperture formed in a face-to-face portion with the fitting portion 38.

A sensor take-out port 35 and a film collecting port 36 are, as illustrated in FIG. 2, formed in a portion on a leading end side of a side wall, facing the slider 15, of the case 31. The sensor take-out port 35 serves as an aperture taking a shape admitting passage of the film-shaped sensor 45. The film collecting port 36 serves as an aperture taking a shape admitting passage of the mount film 41. The sensor take-out port 35 and the film collecting port 36 are provided at an interval shorter than a length of the film-shaped sensor 45. A shape of the side wall of the case 31 is determined so that "the sensor take-out port 35, the film collecting port 36 and a side wall portion existing therebetween" (which are hereinafter referred to as a port unit of the sensor cartridge 30) are recessed slightly more inward than other portions. The side wall portion of the case 31 existing between the sensor take-out port 35 and the film collecting port 36 takes such a shape that at least a part of the mount film 41 is bent at a curvature (at which a part of film-shaped sensor 45 is exfoliated from the mount film 41) equal to or smaller than a predetermined curvature when bending the mount film 41 of the sensor element 40 along the side wall portion.

The case 31 also houses a curved surface wall 39 extending the thicknesswise direction of the case 31. A shape of this curved surface wall 39 is determined so that the sensor element 40 (the mount film 41) entering the portion not provided with the curved surface wall 39 is, as illustrated in FIG. 2, housed in a way of swirling within a film housing space defined by the curved surface wall 39.

The sensor element 40 in the sensor cartridge 30 passes through the sensor take-out port 35 and the film collecting port 36 and is, after being wound along the outer peripheral surf ace of the roller 34, collected within the film housing space. Note that the lead portion is housed within the film housing space in the sensor cartridge 30 before starting the use thereof.

A configuration and functions of the measurement apparatus according to the first embodiment will hereinafter be described.

Figure 6A:
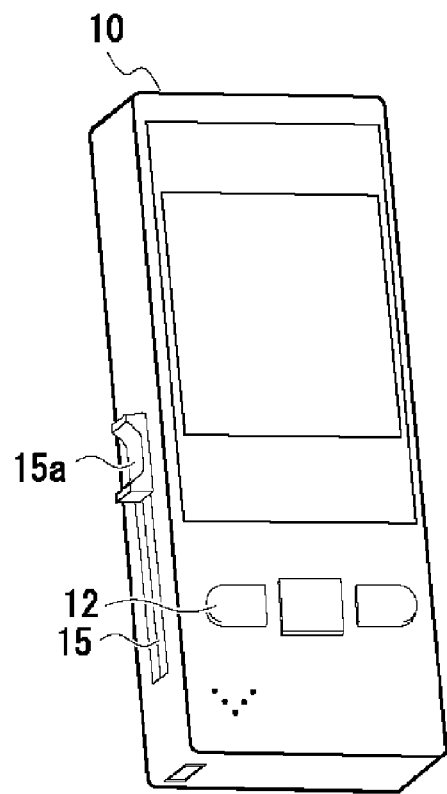
FIGS. 6A and 6B are explanatory views of functions of the measurement apparatus according to the first embodiment.

In the measurement apparatus according to the first embodiment, when in a standby mode (other than when measuring the blood glucose level), the slider knob 15a is located in a position illustrated in FIG. 1 (which will hereinafter be termed a standby position), i.e., located in the vicinity of a center of a slider movable range. The measurement apparatus according to the first embodiment is configured so that the slider knob 15a is, as illustrated in FIG. 6 (A), temporarily slid to an uppermost position (which will hereinafter be termed a sensor take-out position), i.e., the vicinity of one end of the slider movable range, and is thereafter, as illustrated in FIG. 6 (B), slid to a lowermost position (which will hereinafter be terms a measurement position), i.e., the end, vicinal to the aperture of the enclosure 10, of the slider movable range, with the result that the slider 15 and an auxiliary slider 18 protrude from an aperture (which will hereinafter be termed a slider protrusion port) formed in the enclosure 10 in a state of the film-shaped sensor 45 being pinched between tips of these sliders.

At first, a mechanical configuration of the measurement apparatus functioning when sliding the slider knob 15a to the sensor take-out position, will be described.

Figure 7:
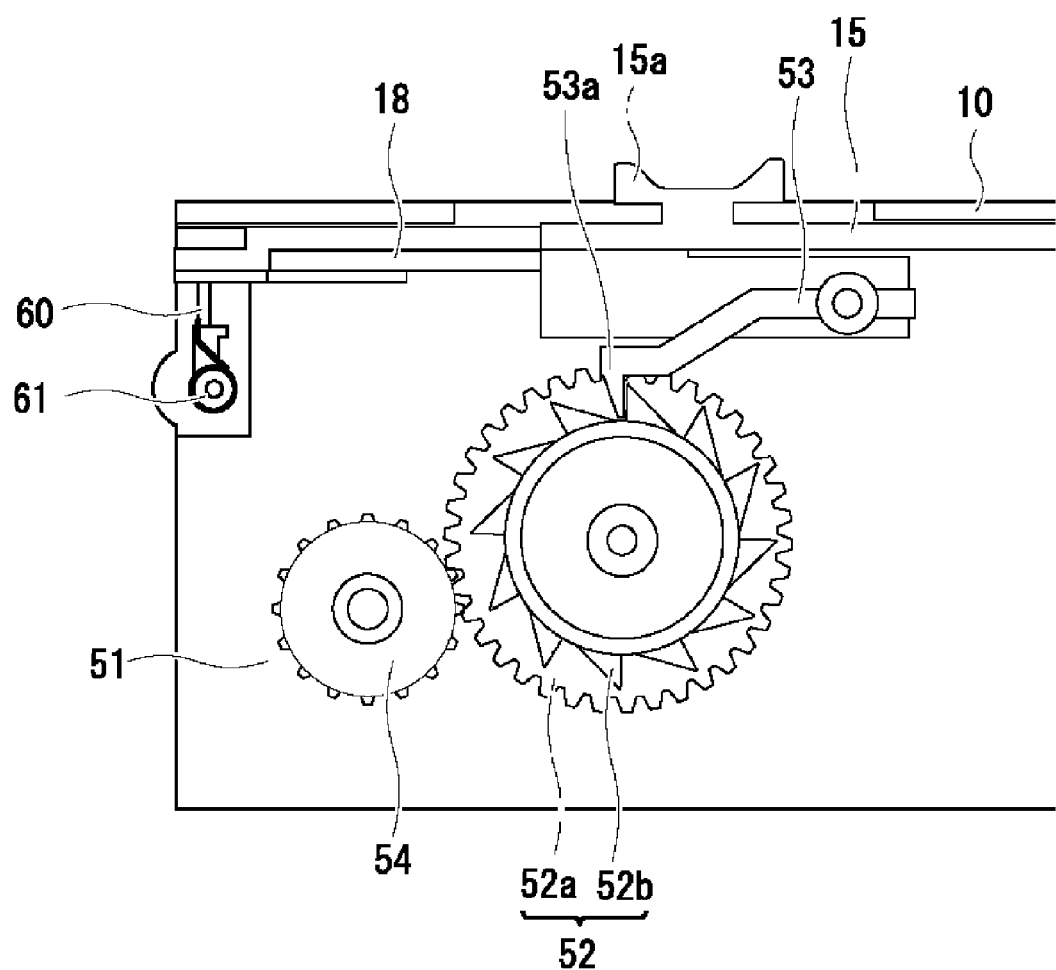
FIG. 7 is a sectional view taken in parallel to a front surface in the vicinity of the front side of the measurement apparatus according to the first embodiment.

FIG. 7 illustrates a sectional view taken in parallel to the front surface in the vicinity of the front side of the measurement apparatus according to the first embodiment.

As depicted in FIG. 7, the measurement apparatus includes a partition plate 51, a composite gear 52, a pawl member 53 and a driving gear 54. The partition plate 51 is a plate member with the sensor cartridge 30 being set on its undersurface (a surface on an invisible side in FIG. 7). The driving gear 54 is secured to the partition plate 51 so as to be rotatable about a rotary shaft thereof. The rotary shaft of the driving gear 54 is provided to penetrate the partition plate 51 in such a position as to be concentric with the fitting portion 38 of the roller 34 of the sensor cartridge 30 set in the enclosure 10. The rotary shaft of the driving gear 54 takes a shape matching with the fitting portion 38 (see FIG. 5) of the roller 34 of the sensor cartridge 30 when the sensor cartridge 30 is set therein.

The composite gear 52 is configured to include a general gear 52 and a general ratchet wheel 52b that are superposed in alignment of centers of rotations thereof. The composite gear 52 is rotatably secured to the partition plate 51. The rotary shaft of the composite gear 52 is positioned so that the gear 52a meshes with the driving gear 54. The pawl member 53 is a member fixed to the slider 15. The pawl member 53 includes a pawl 53a taking such a shape as to mesh with the ratchet wheel 52b of the composite gear 52 when the slider 15 is located in the standby position.

The shapes of the respective portions of the measurement apparatus according to the first embodiment and/or a moving distance from the standby position of the slider 15 to a take-out completing position (measurement position), are determined to satisfy the following two conditions.

[Condition 1] To attain a state where the slider 15 does not exist on the sensor take-out port 35 when the slider 15 moves to the sensor take-out position.

[Condition 2] To attain coincidence between "a value given by multiplying a radian angle of rotation of the roller 34 by a radius of the roller 34" and a value of the sensor disposing interval of the sensor element 40 (a value of the intervals between centers of the two adjacent film-shaped sensors 45 of the sensor element 40) when the slider 15 moves to the sensor take-out position from the standby position.

Figure 8:
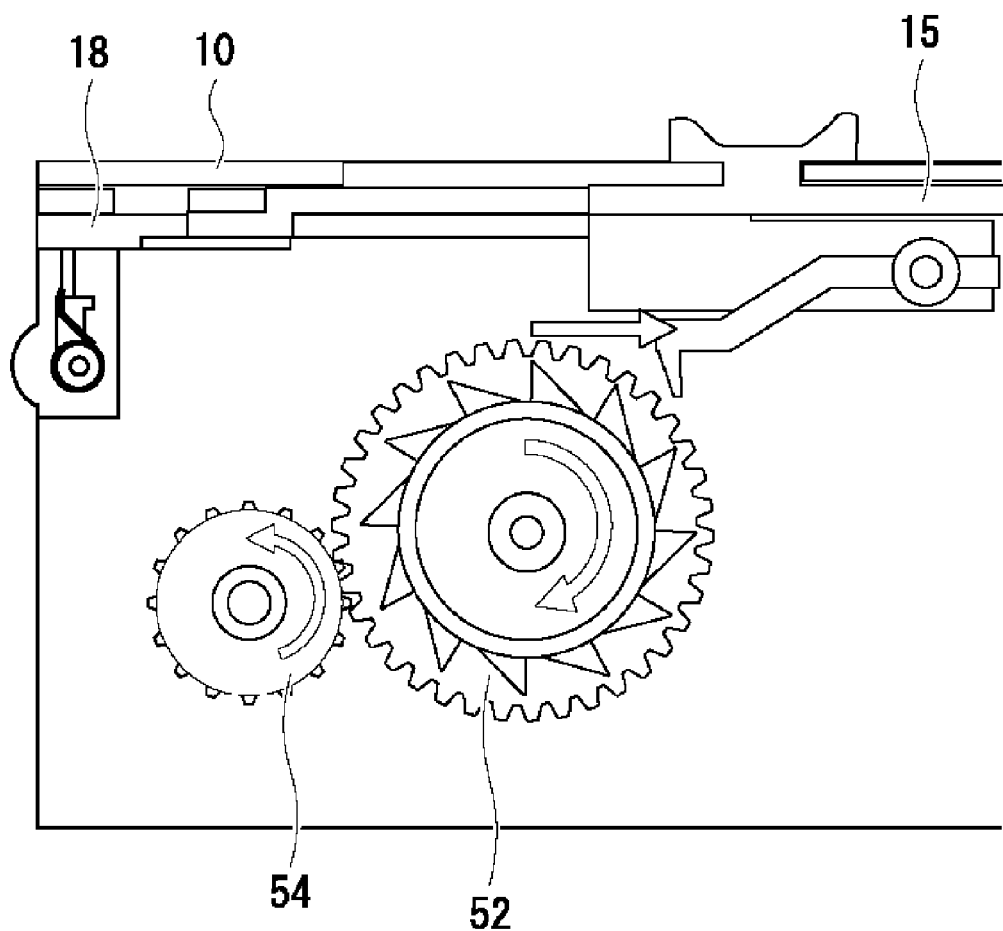
FIG. 8 is an explanatory view of operations of respective units of the measurement apparatus according to the first embodiment.

In short, as illustrated in FIG. 8, when the slider 15 moves to the sensor take-out position from the standby position by operating the slider knob 15a, the composite gear 52 rotates clockwise, while the driving gear 54 rotates counterclockwise. The rotary shaft of the driving gear 54 is fitted to the fitting portion 38, and hence the roller 34 rotates counterclockwise through the same angle as the angle of the driving gear 54. Accordingly, when determining the shapes and other equivalent data of the respective portions to attain the coincidence between "the value given by multiplying the radian angle of rotation of the roller 34 by the radius of the roller 34" and the value of the sensor disposing interval of the sensor element 40 when the slider 15 moves to the sensor take-out position from the standby position, the sensor element 40 within the sensor cartridge 30 can be fed by "the sensor disposing interval" in the direction of each film-shaped sensor 45 advancing toward the sensor take-out port 35.

Figure 9:
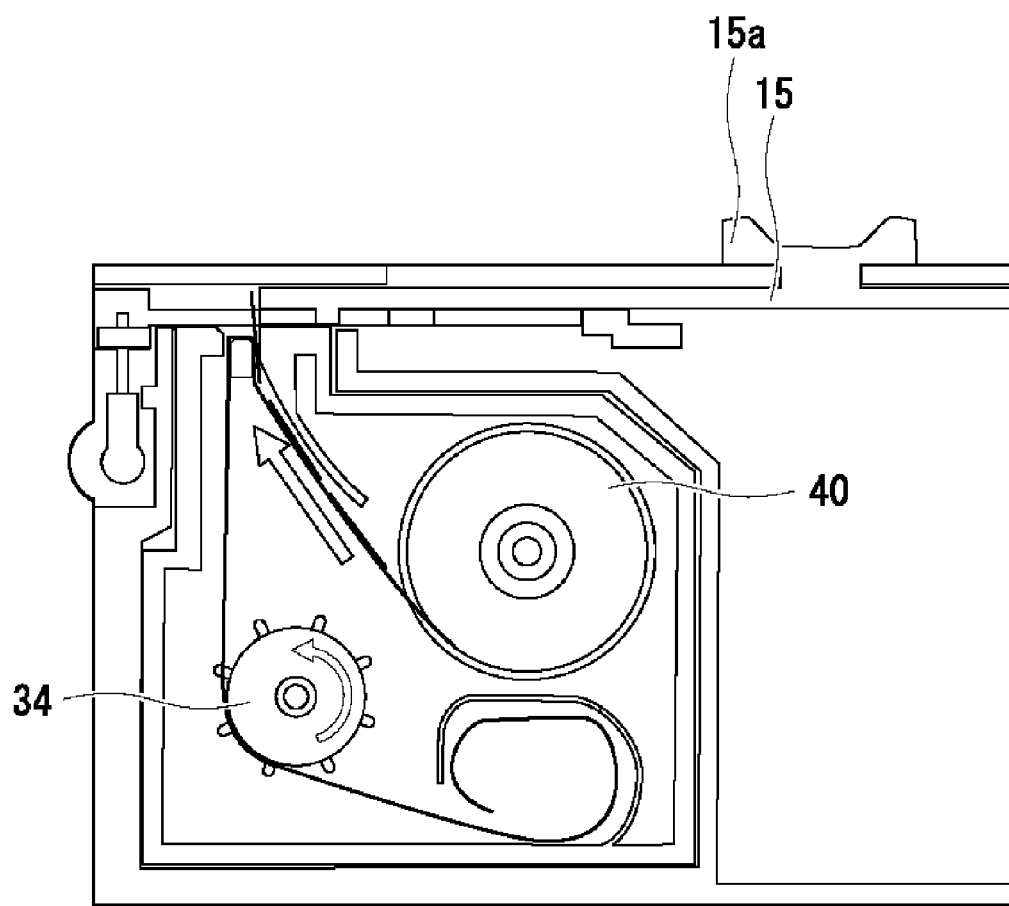
FIG. 9 is an explanatory view of the operations of the respective units of the measurement apparatus according to the first embodiment.
Figure 10:
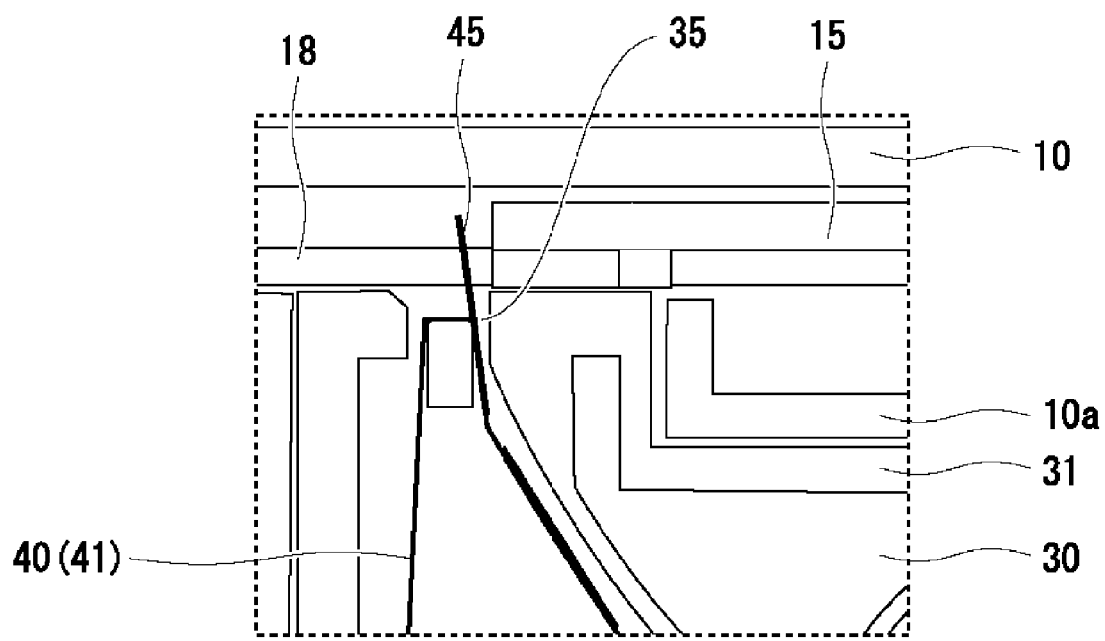
FIG. 10 is an explanatory view of the operations of the respective units of the measurement apparatus according to the first embodiment.

When the sensor element 40 is bent so that the surface, on which the film-shaped sensor 45 is disposed, of the sensor element 40 becomes convex, the film-shaped sensor 45 is exfoliated from the mount is exfoliated from the mount film 41. The sensor element 40 is consequently fed by "the sensor disposing interval". Upon reaching substantially 90-degree bending of the fed portion of the mount film 41 in the vicinity of an outlet of the sensor take-out port 35, the film-shaped sensor 45 adhered to the bent portion is exfoliated from the mount film 41. It follows then that the film-shaped sensor 45 protrudes from the sensor take-out port 35 as illustrated in FIGS. 9 and 10.

However, if the slider 15 is located above the sensor take-out port 35 when the film-shaped sensor 45 protrudes from the sensor take-out port 35, the slider 15 cannot carry the film-shaped sensor 45 protruding from the sensor take-out port 35. Therefore, the shapes and other equivalent data of the respective portions of the measurement apparatus are determined to satisfy the condition 1.

Next, a mechanical configuration of the measurement apparatus functioning when the slider knob 15a is slid to the measurement position from the sensor take-out position, will hereinafter be described.

Figure 11:
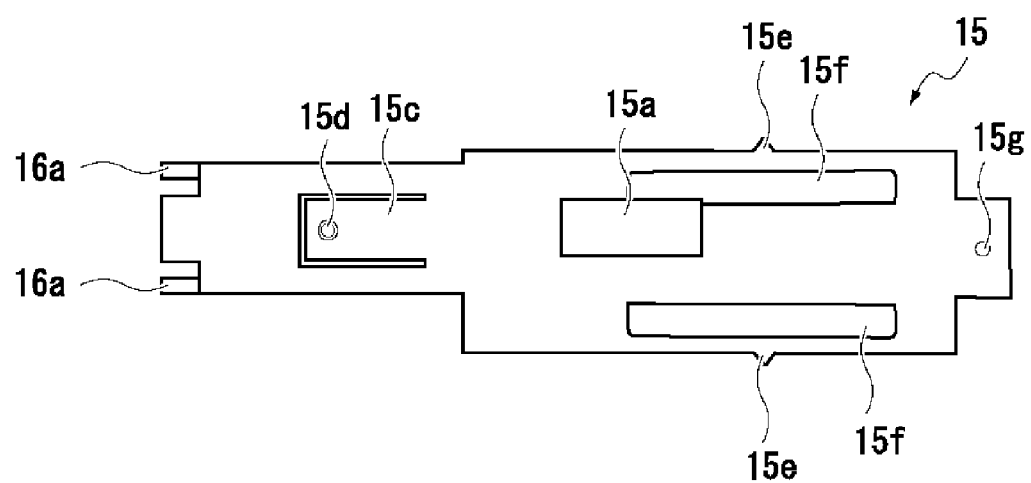
FIG. 11 is a view of an external appearance of a slider as viewed from the side of an upper surface.
Figure 12:
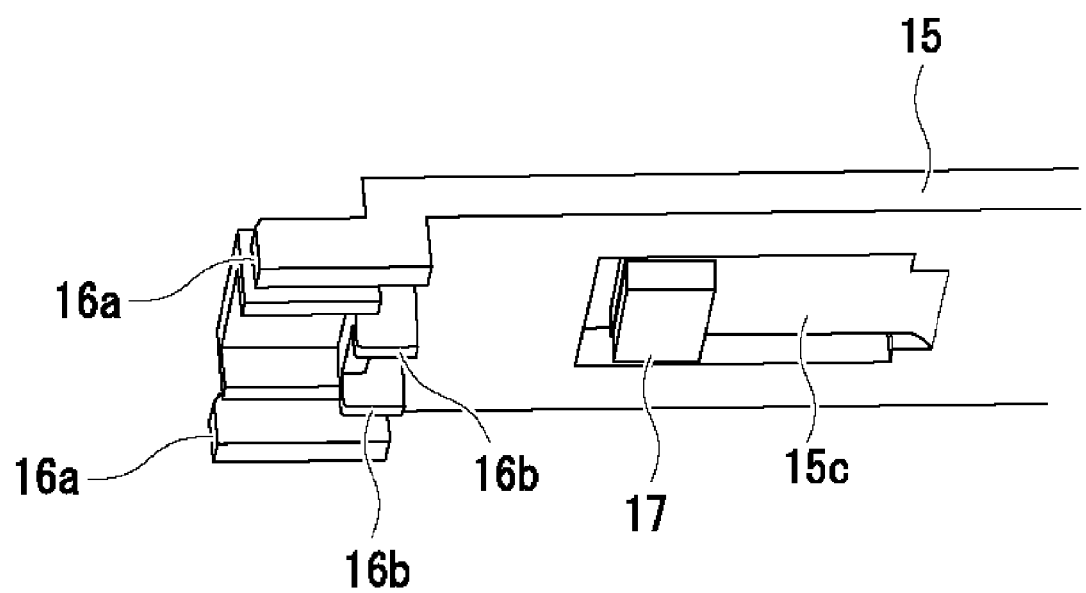
FIG. 12 is a view of an external appearance of the slider as viewed from the side of a lower surface.

FIG. 11 depicts a view of an external appearance of the slider 15 as viewed from the side of an upper surface (provided with the slider knob 15a). FIG. 12 illustrates a view of the external appearance of the slider 15 as viewed from the undersurface.

As illustrated in FIG. 12, two protrusions 16b for extruding forward the film-shaped sensor 45 protruding from the sensor take-out port 35 of the sensor cartridge 30, are provided at the center of the leading end of the slider 15. As depicted in FIGS. 11 and 12, structures 16a having shapes matching with structures provided at the leading end of the auxiliary slider 18 are provided on both sides of the leading end of the slider 15. The auxiliary slider 18 is herein disposed within the enclosure 10 to move together with the slider 15 as far as the slider 15 is located between the standby position and the measurement position.

Figure 6B:
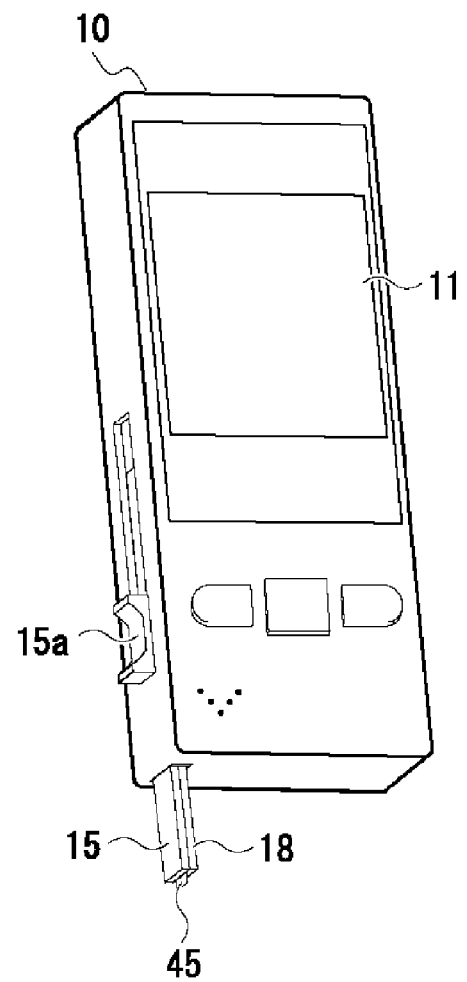

A leading end of the auxiliary slider 18 is provided with a structure to pinch the film-shaped sensor in between the leading end of the slider 15 and the leading end of the auxiliary slider 18 in addition to the structure engaging with the structure 16a. When the slider 15 moves to the measurement position from the sensor take-out position by operating the slider knob 15a, at first, the film-shaped sensor 45 is extruded forward by the two protrusions 16b of the slider 15. Subsequently, the structure 16a provided at the leading end of the slider 15 is fitted to the structure provided at the leading end of the auxiliary slider 18, thereby forming a state of the film-shaped sensor 45 being pinched in between the leading end of the slider 15 and the leading end of the auxiliary slider 18 and also a state of the auxiliary slider 18 moving together with the slider 15. Then, these states remaining unchanged, when the slider 15 and the auxiliary slider 18 complete sliding to the measurement position of the slider knob 15a, as illustrated in FIG. 6(B), the film-shaped sensor 45 is held by the slider 15 and the auxiliary slider 18.

Figure 13:
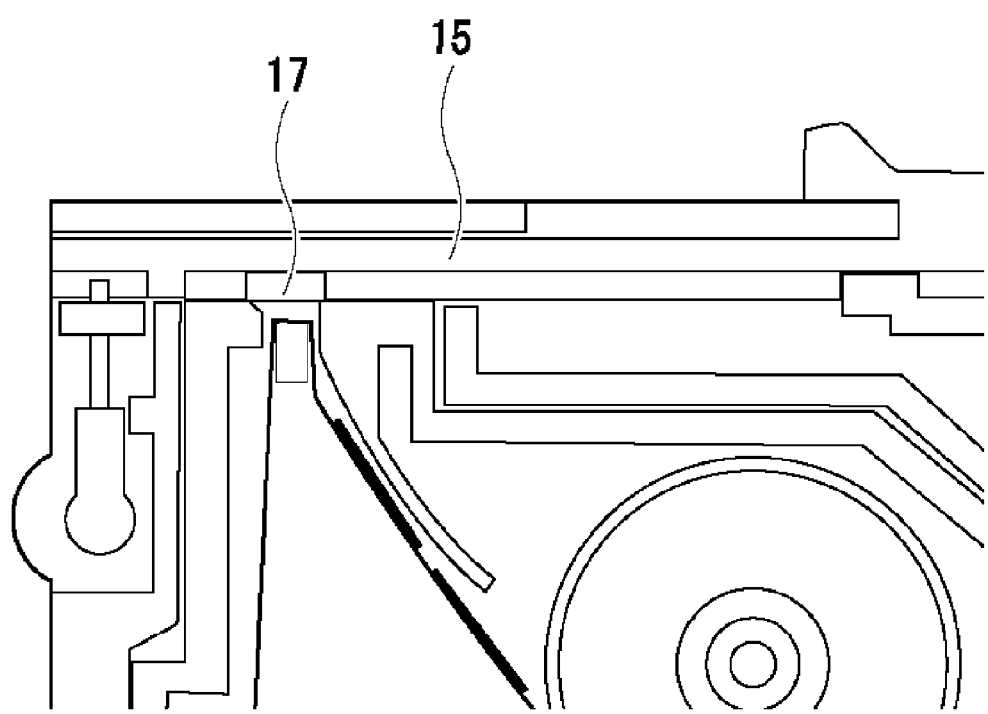
FIG. 13 is an explanatory view of a position of attaching a sealing rubber.

As depicted in FIGS. 11 and 12, the slider 15 includes a flexural portion 15c formed to enable the leading end (the left side in each drawing) to move vertically. A sealing rubber 17 is attached to an undersurface of the flexural portion 15c on the side of a leading end thereof. A position and a shape of the flexural portion 15c and a shape of the sealing rubber 17 are determined so that the sealing rubber 17, as illustrated in FIG. 13, is located above a port portion (configured by the sensor take-out port 35, the film collecting port 36 and a side wall therebetween) of the sensor cartridge 30 at least when the slider 15 is located in the standby position. Note that the sealing rubber 17 may take a shape of flat sheet and preferably the same or similar shape as or to the shape of the port portion of the sensor cartridge 30.

As illustrated in FIG. 11, a protruded portion 15d taking a shape of circular truncated cone is provided at a portion, corresponding to substantially the center of the sealing rubber 17, of an upper surface of the flexural portion 15c. A hole 15g is formed in the central portion of the slider 15 on a tail end side (the right side in FIG. 11). A protruded portion 15e protruding in the widthwise direction is provided on each side surface of the slider 15 in the widthwise direction. The slider 15 is formed with an aperture 15f for facilitating displacement of each protruded portion 15e in the widthwise direction of the slider 15.

Figure 14:
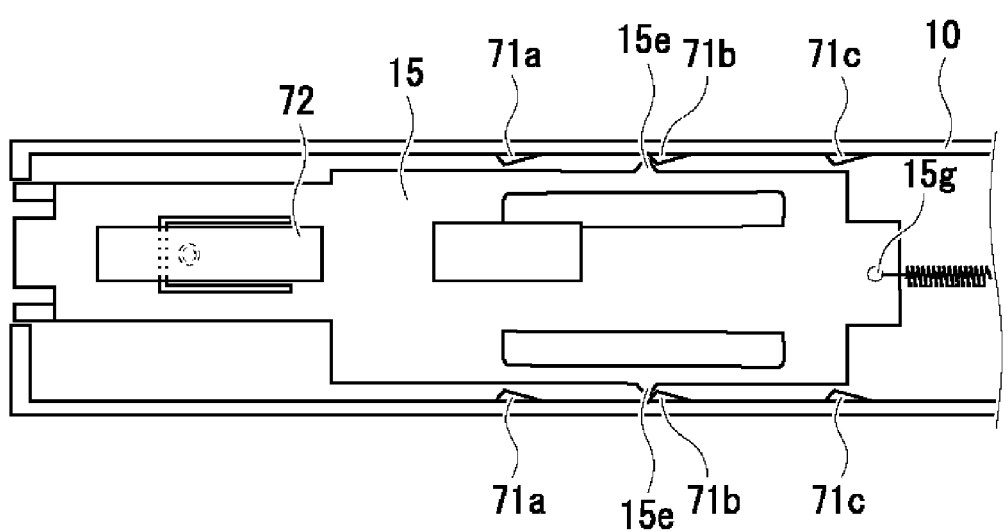
FIG. 14 is an explanatory view of a configuration of the measurement apparatus according to the first embodiment.

A coil spring establishes, as illustrated in FIG. 14, a connection between the hole 15g of the slider 15 and a specified portion within the enclosure 10. Three-tuple protruded portions 71x (x=a through c) are provided in positions depicted in FIG. 14 within the enclosure 10. To be specific, a couple of protruded portions 71a are provided within the enclosure 10, the protruded portions 71a serving to stop the slider 15 biased by the coil spring in the measurement position by engaging with a couple of protruded portions 15e of the slider 15. A couple of protruded portions 71b are further provided within the enclosure 10, the protruded portions 71b serving to stop the slider 15 in the standby position by engaging with the couple of protruded portions 15e of the slider 15. A couple of protruded portions 71c are still further provided within the enclosure 10, the protruded portions 71c serving to stop the slider 15 in the sensor take-out position by engaging with the couple of protruded portions 15e of the slider 15.

A biasing means (a plate spring in FIG. 14) 72 is provided at a face-to-face portion with the protruded portion 15d of the slider 15 located in the standby position, the biasing means serving to push up the protruded portion 15d toward the port portion of the sensor cartridge 30. As already described, the sealing rubber 17 is provided on the underside of the protruded portion 15d. Therefore, when the slider 15 is located in the standby position, it follows that the port portion of the sensor cartridge 30 is sealed by the sealing rubber 17.

Figure 15:
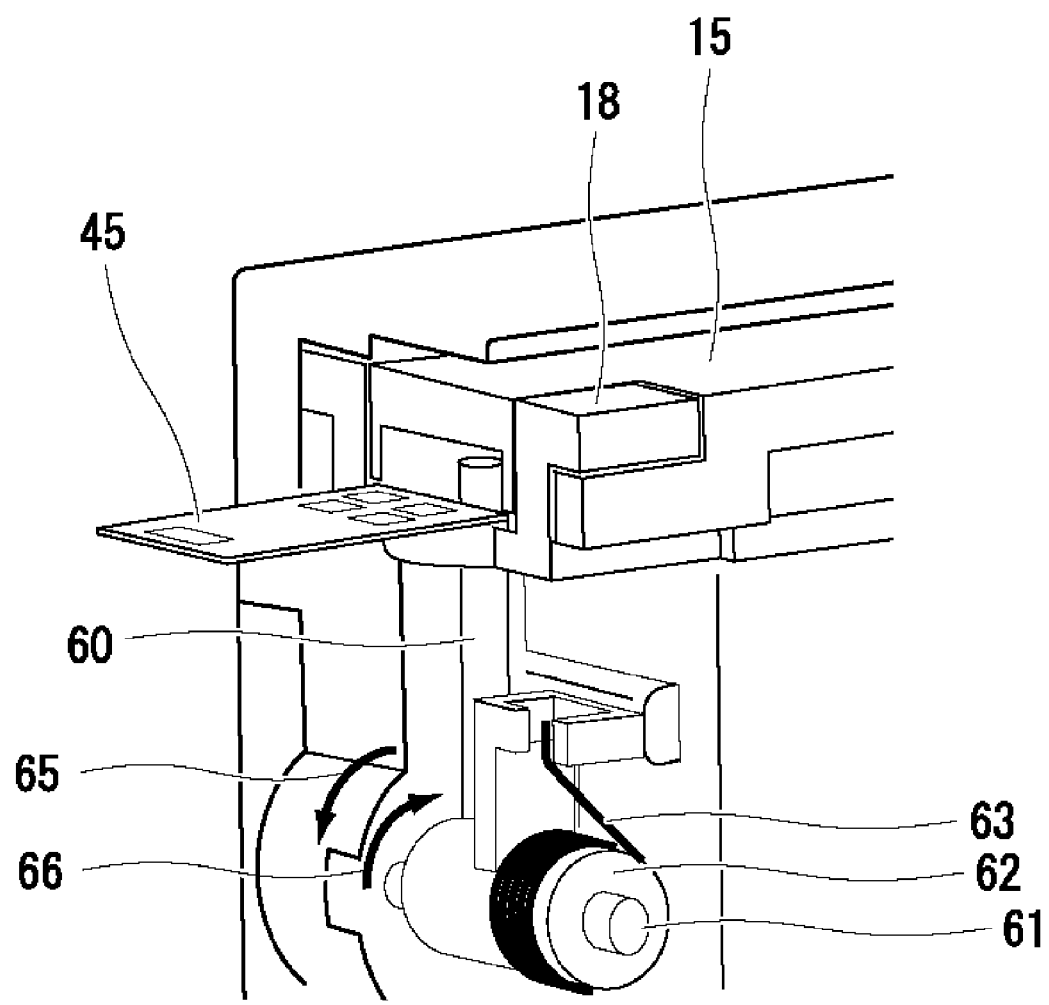
FIG. 15 is an explanatory view of a configuration of a sensor discard mechanism included in the measurement apparatus according to the first embodiment.

As illustrated in FIG. 15, a sensor discard mechanism is provided in the vicinity of a slider protrusion port (the aperture from which the slider 15 and the auxiliary slider 18 protrude) of the enclosure 10 of the measurement apparatus, the sensor discard mechanism including a discard pin 60, a rotary shaft 61, a rotary member 62 and a biasing member 63. The discard pin 60 of the sensor discard mechanism is fixed to the enclosure 10 and is parallel to the widthwise direction of the slider 15. The rotary member 62 rotates about the rotary shaft 61. The discard pin 60 is a rod-shaped member fixed to the rotary member 62 so as to be orthogonal to the rotary shaft 61. The biasing member 63 (the coil spring in FIG. 15) biases the discard pin 60 via the rotary member 62 in such a direction that the discard pin 60 becomes parallel to the undersurface of the enclosure 10.

As illustrated in FIG. 15, a length of the discard pin 60 of the sensor discard mechanism is determined so as to intersect a moving plane of the film-shaped sensor 45 in a state of being pinched in between the slider 15 and the auxiliary slider 18 when in parallel to the undersurface of the enclosure 10. A length of the discard pin 60 is further determined so as not to contact the respective portions (the portion existing between the two protrusions 16b, and other equivalent portions; see FIG. 12) of the slider 15. The leading end of the auxiliary slider 18 is formed with a groove through which the discard pin 60 passes.

In short, the discard pin 60 of the sensor discard mechanism is pushed by the film-shaped sensor 45 and falls down (see an arrowhead 65) when the film-shaped sensor 45 comes out of the slider protrusion port, and reaches a state in which a tip of this pin 60 slides on the undersurface of the film-shaped sensor 45. The discard pin 60 is, however, biased by the biasing member 63. Accordingly, once the film-shaped sensor 45 passes by, the discard pin 60 rises (see an arrowhead 66), and, as a result, such a state occurs that the tip of the discard pin 60 enters the auxiliary slider 18 and the slider 15. In this state, upon an operation to return the slider 15 to the standby position, the film-shaped sensor 45 used for the measurement abuts on the discard pin 60 before the slider 15 reaches the standby position. Then, the film-shaped sensor 45, upon abutting on the discard pin 60, comes to a state being disabled from moving, however, the slider 15 and the auxiliary slider 18 are slidable even when the discard pin 60 is erected. It therefore follows that the already-used film-shaped sensor 45 can be discarded simply by returning the position of the slider knob to the standby position after measuring the blood glucose level in the measurement apparatus including the sensor discard mechanism according to the first embodiment.

Next, an electrical configuration of the measurement apparatus will be described.

Figure 16A:
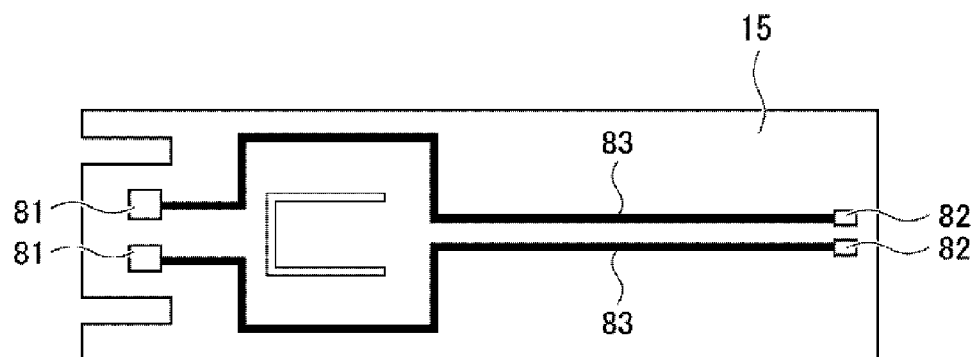
FIGS. 16A and 16B are explanatory views of an electrical configuration of the measurement apparatus according to the first embodiment.

An electrical configuration (circuit configuration) of the measurement apparatus according to the first embodiment is the same as the electrical configuration of the existing apparatus for measuring the blood glucose level and other equivalent measurement targets. The measurement apparatus according to the first embodiment is, however, configured to connect the film-shaped sensor 45 to the tip of the moving slider 15. The slider 15 is therefore provided with wires and other equivalent components for connecting the respective electrodes of the film-shaped sensors 45 to corresponding electrodes of the control unit 14 within the measurement apparatus. For example, when the film-shaped sensor 45 includes the two electrodes, as schematically illustrated in FIG. 16(A), the undersurface of the slider 15 is provided with electrodes 81 brought into contact with the respective electrodes of the film-shaped sensor 45, electrodes 82 connected to the control unit 14 (FIG. 16(B)) within the measurement apparatus and wires 83 for establishing connections between the electrodes 81 and the electrodes 82. Herein, the control unit 14 is a circuit using a processor (one-chip microcomputer and other equivalent processors) executing a process of measuring an oxidation reduction potential about the film-shaped sensor 45, a process of calculating the blood glucose level from a measurement result, and a process of controlling an LCD 11 (unillustrated) and the speaker 13. Note that the electrodes and the wires can be provided on the undersurface of the slider 15 by printing conductive materials on the undersurface of the slider 15, making use of in-mold forming (integrally molding the slider 15 and the electrodes/wires) and printing the conductive materials on the upper surface of the slider 15. The electrode 81 may also involve using a plate spring type electrode and a pin probe.

Figure 16B:
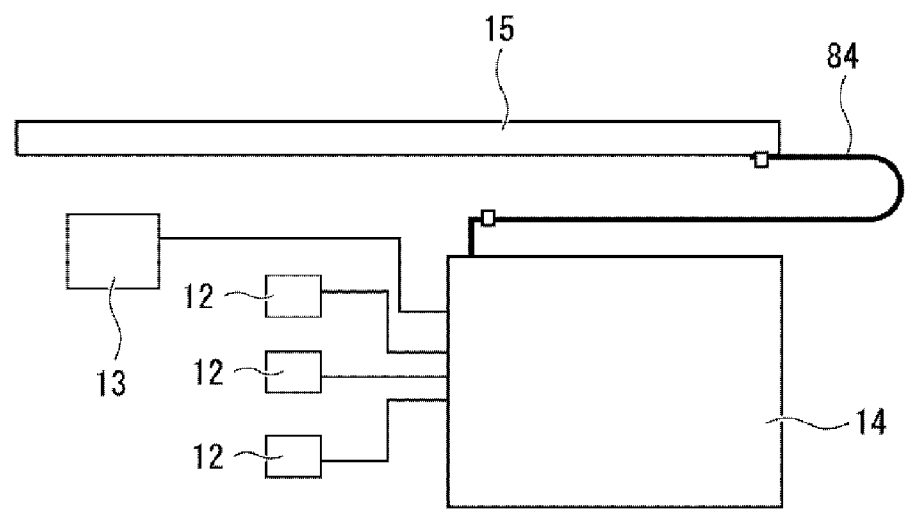

The measurement apparatus according to the first embodiment is configured so that the position of the slider 15 shifts within the apparatus, and hence it is considered that lead wires are entangled in the members within the measurement apparatus and result in being cut off when the respective electrodes 82 are connected via the lead wires to the control unit 14. Therefore, as schematically illustrated in FIG. 16(B), it is preferable that the electrodes 82 are connected to the control unit 14 by use of a flexible printed circuit board 84 or other equivalent components.

Each wire 83 (or each electrode 82) of the slider 15 may be configured to have a long portion parallel to the lengthwise direction of the slider 15; the enclosure-sided electrode may be fixed to the enclosure 10 to contact the wire 83 (or the electrode 82) irrespective of the position of the slider 15 per wire 83 (or per electrode 82); and the enclosure-sided electrode fixed to the enclosure 10 may be electrically connected to the control unit 14 via a cable or other equivalent connectors. The length of each wire 83 or each electrode 82 of the slider 15 and the position of the enclosure-sided electrode may be set so that each wire 83 or each electrode 82 contacts each enclosure-sided electrode as far as the slider 15 is located in the vicinity of the measurement position.

As discussed above, the respective film-shaped sensors 45 are disposed on the central portion, excluding the edge portions in the widthwise direction, of the mount film 41, and the sensor element 40, which can be therefore easily manufactured, is used in the reel hub 32 within the sensor cartridge 30 set in the measurement apparatus according to the first embodiment. The sensor element 40 is configured so that the end portion of the film-shaped sensor 45 is exfoliated from the mount film 41 by bending the portion, under the end portion of a certain film-shaped sensor 45, of the mount film 41 at the curvature equal to or smaller than the predetermined curvature in a longitudinal direction of the sensor element 40 with such a posture as to direct inward the undersurface of the mount film 41. The wall of the case 31, which exists between the sensor take-out port 35 and the film collecting port 36, takes such a shape that at least a part of the mount film 41 is bent at the curvature equal to or smaller than the predetermined curvature when bending the mount film 41 of the sensor element 40 along the wall. Accordingly, when rotating the roller 34 of the sensor cartridge 30, a part of the film-shaped sensor 45 is exfoliated from the mount film 41 in the vicinity of the sensor take-out port 35 and protrudes from the sensor cartridge 30 (the sensor take-out port 35).

The film-shaped sensor 45, apart of which protrudes from the sensor cartridge 30, can be taken out of the sensor cartridge 30 with a simple mechanism. The measurement apparatus according to the first embodiment therefore has the simple configuration (including the small number of components) described above.

A description of a configuration of a sensor cartridge 30b developed to be set in the measurement apparatus according to the first embodiment will hereinafter be made with reference to FIG. 17 in a way of focusing on portions different from the sensor cartridge 30.

Figure 17:
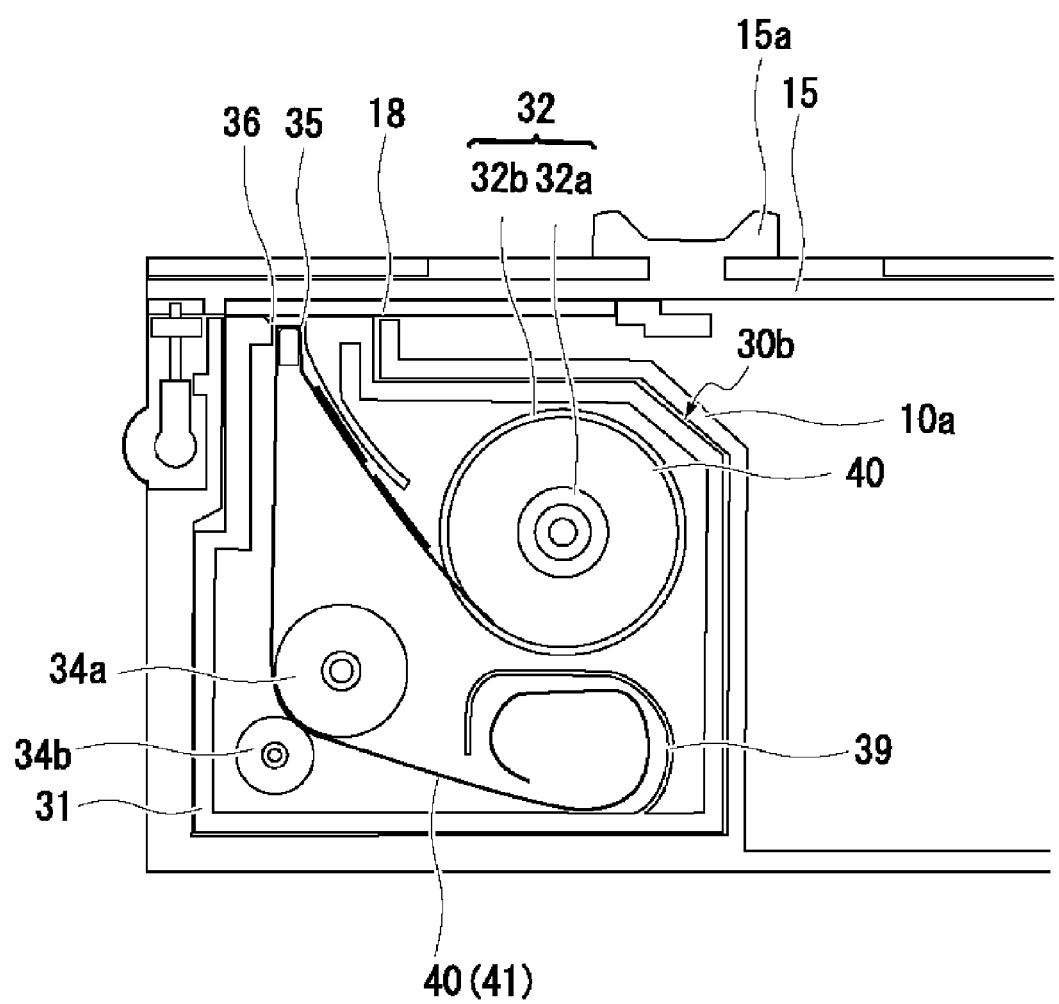
FIG. 17 is an explanatory view of a configuration of a sensor cartridge that can be set in the measurement apparatus according to the first embodiment.

As apparent from a comparison between FIG. 17 and FIG. 2, the sensor cartridge 30b has a configuration to replace the roller 34 of the sensor cartridge 30 with a roller 34a and a roller 34b.

The roller 34a does not include the plurality of pins provided on the external surface thereof. The roller 34b is a so-called pinch roller for press-fitting the mount film 41 onto the roller 34a.

In short, the sensor cartridge 30b has the configuration enabling a use of the sensor element 40 not formed with the holes 42 (FIG. 3). It can be therefore said that the sensor cartridge 30b therefore exhibits the same operational effect as the effect of the sensor cartridge 30 and can be manufactured at a lower cost than manufacturing the sensor cartridge 30 to such a degree as to eliminate a necessity for the process of forming the holes 42.

<<Second Embodiment>>

A configuration of the measurement apparatus according to a second embodiment of the present invention will be described by focusing on portions different from the measurement apparatus according to the first embodiment.

Figure 18:
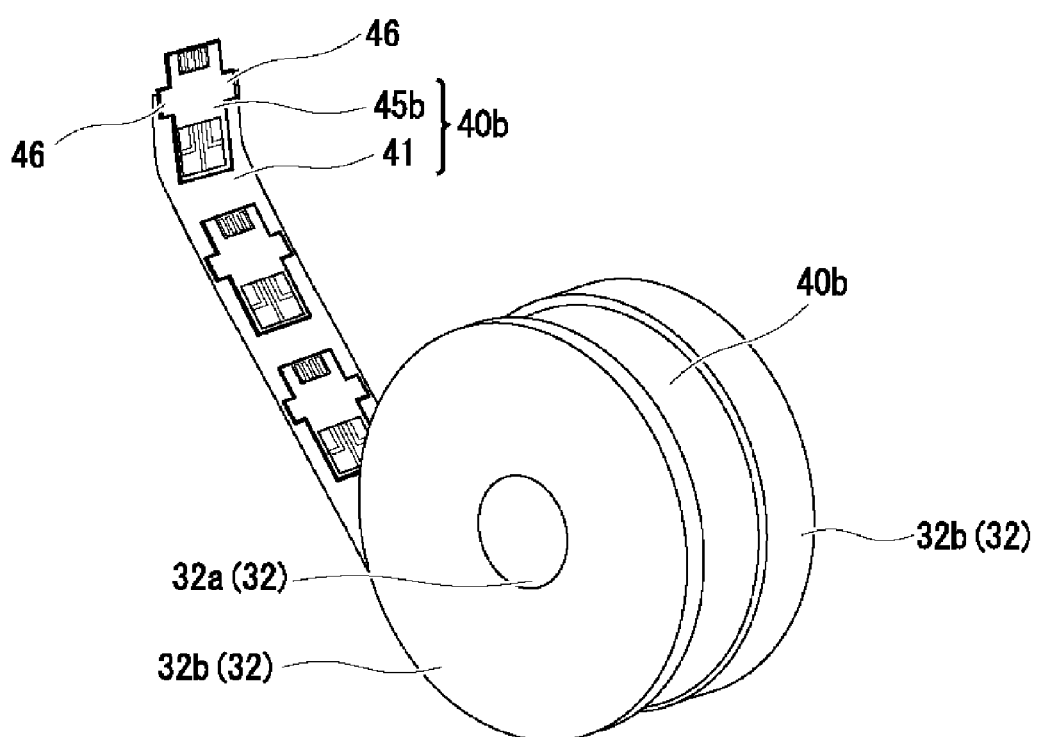
FIG. 18 is an explanatory view of a configuration of a sensor element used in the cartridge that is set in the measurement apparatus according to a second embodiment of the present invention.

The sensor cartridge according to the second embodiment, which is set in the measurement apparatus according to the second embodiment, is configured to include a sensor element 40b that replaces the sensor element 40 within the sensor cartridge 30b (FIG. 17), the sensor element 40b having a configuration illustrated in FIG. 18. The measurement apparatus according to the second embodiment of the present invention is configured as an apparatus different in terms of only the shape of the leading end of the slider 15 from the measurement apparatus according to the first embodiment.

To be specific, as depicted in FIG. 18, the sensor element 40b within the sensor cartridge according to the second embodiment is configured so that a plurality of film-shaped sensors 45b is provided with protruded portions 46 being slightly closer to the leading end than the central portion of both edges in the widthwise direction and is bonded onto the mount film 41 to parallelize the widthwise direction of each film-shaped sensor 45b and the widthwise direction of the mount film 41.

Each film-shaped sensor 45b taking the shape described above, the film-shaped sensor 45b protrudes from the sensor take-out port 35 of the sensor cartridge according to the second embodiment in a state of each protruded portion 46 being exfoliated from the mount film 41 (i.e., a state of enabling the member to be inserted under the lower edge of each protruded portion 46).

When setting beforehand the member to be inserted under the lower edge of each protruded portion 46 of the film-shaped sensor 45b protruding from the sensor take-out port 35, and even when the shape of the slider 15 and a positional relation between the respective portions are slightly different from a shape in design and a positional relation in design due to a manufacturing error or other equivalent errors, a part thereof enables the film-shaped sensor 45b adhered to the mount film 41 to be exfoliated form the mount film 41 and held by the slider 15.

The shape of the leading end of the slider 15 of the measurement apparatus according to the second embodiment is therefore designed so that the slider 15 can exfoliate the film-shaped sensor 45b from the mount film 41 and can hold the film-shaped sensor 45b by engaging with the lower edges of the two protruded portions 46 of the film-shaped sensor 45b protruding form the sensor take-out port 35.

<<Modified Mode>>

The variety of technologies described above may be modified in multiple modes. For example, the sensor element 40b illustrated in FIG. 18 may be modified into a sensor element formed with the holes at the sensor disposing interval as in the case of the sensor element 40 depicted in FIG. 3. Each sensor cartridge may also contain a desiccant beforehand.

The measurement apparatus according to each of the first and second embodiments includes the film-shaped sensor 45 protruding in the state of being pinched in between the slider 15 and the auxiliary slider 18. Each measurement apparatus may, however, be modified into an apparatus not including the auxiliary slider 18. Note that the modification of each measurement apparatus into the apparatus not including the auxiliary slider 18 can be attained by adopting, e.g., a configuration given below. A connector is provided at the leading end of the slider 15, the connector enabling the film-shaped sensor 45 to be fixed by inserting the film-shaped sensor 45 and enabling an electric connection to be established between the film-shaped sensor 45 and the control unit 14. Flexibility is given beforehand to the leading end (in the vicinity of the connector) of the slider 15. The measurement apparatus is provided beforehand with a biasing mechanism for moving the leading end of the slider 15 toward the sensor cartridge 30 when passing above the sensor take-out port 35.

Figure 19:
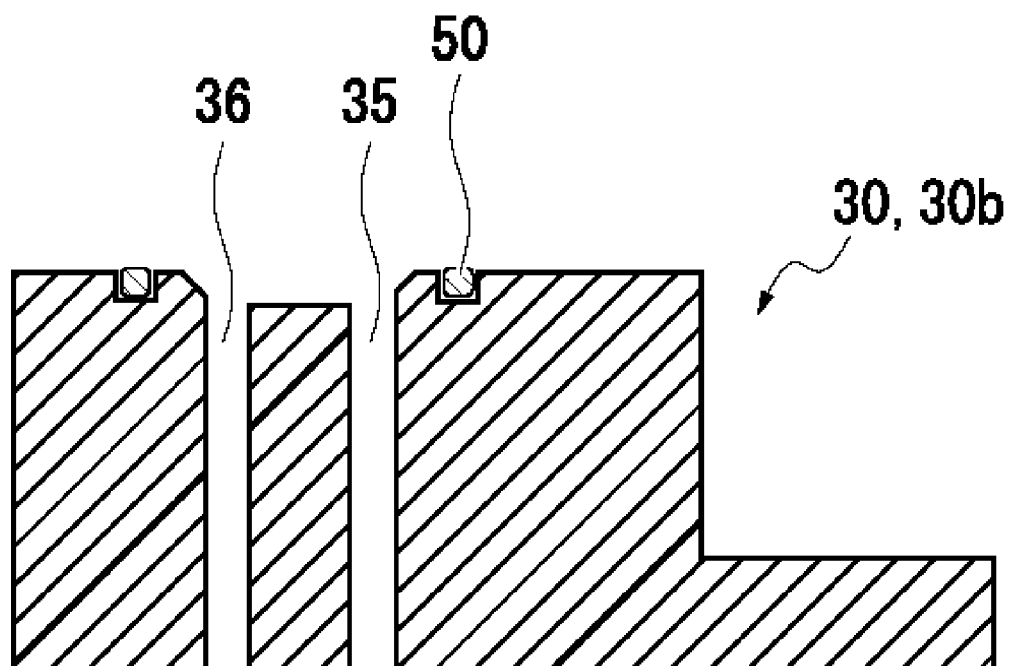
FIG. 19 is an explanatory view of a technology adoptable for bettering a sealing property of the sensor cartridge.

An elastic member 50 taking a shape of closed curve may also be, as schematically illustrated in FIG. 19, disposed to surround the port portion of each of the sensor cartridges 30, 30b in order for the sealing rubber 17 to seal (hermetically close) the sensor cartridges 30, 30b further preferably.

Figure 20:
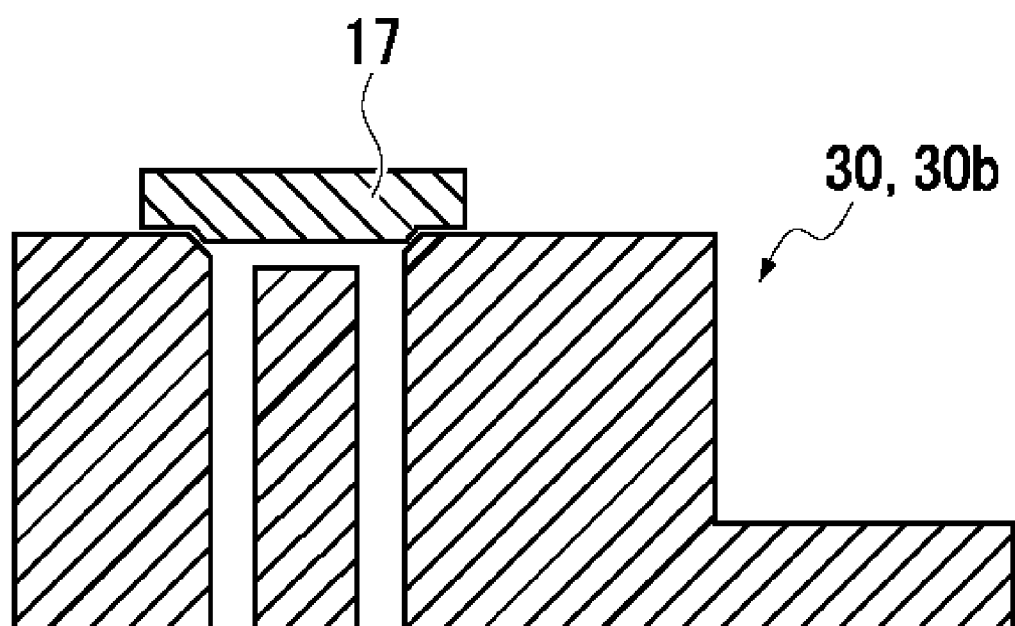
FIG. 20 is an explanatory view of another technology adoptable for bettering the sealing property of the sensor cartridge.

In order to seal the sensor cartridges 30, 30b further preferably, as schematically illustrated in FIG. 20, the sealing rubber 17 may involve adopting a sealing rubber taking such a shape as to fit to the port portion of each of the sensor cartridges 30, 30b. When the fitting portion has an excessively large length, however, the slider 15 becomes hard to slide. When adopting the sealing rubber 17 taking the shape described above, it is preferable for attaining this that the length of the fitting portion is set not to become excessively large.

The sensor element (40, 40b) described above is the sensor element from which the portions other than the film-shaped sensors 45 are removed after being half cut, however these portions are continuous and are not therefore exfoliated from the mount film 41 even when bending the sensor element. The portions not exfoliated from the mount film 41 do not become obstacles against taking out the film-shaped sensor 45 from the sensor element. Hence, not the element of which the portions other than the film-shaped sensors 45 are removed but an element manufactured at a stage of completing the half-cut midway of the adhesive sheet (the element of which the portions other than the film-shaped sensors 45 are not removed) may also be used as the sensor element.

Some functions may also be removed from the measurement apparatus/sensor cartridge described above. It is a matter of course that the measurement apparatus/sensor cartridge may be modified into an apparatus/cartridge for measuring some physical quantities related not to the blood but to measurement objects.

Figure 21:
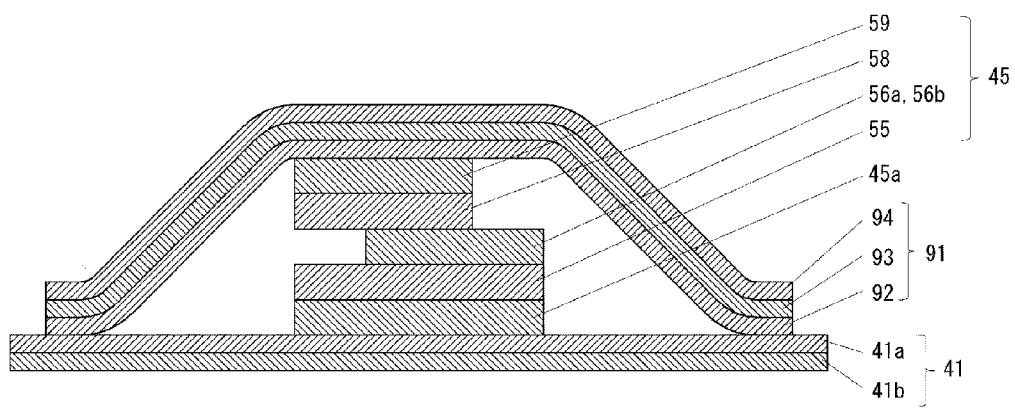
FIG. 21 is a sectional view of a modified example of the sensor element.
Figure 22:
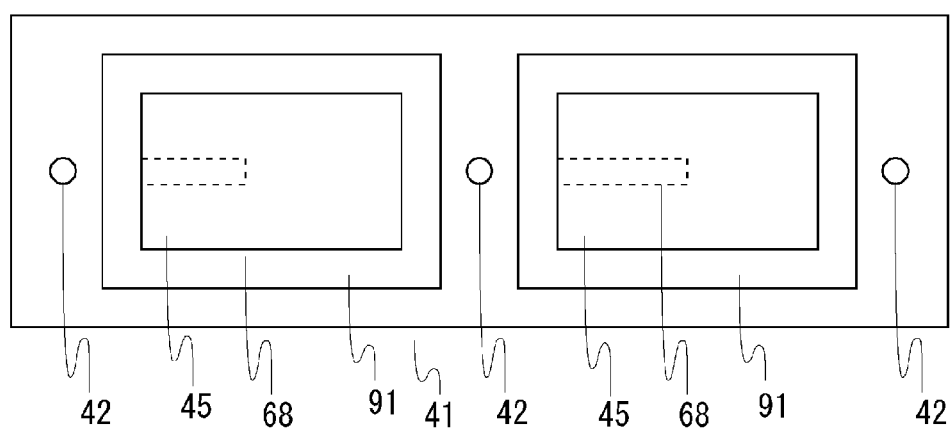
FIG. 22 is a top view of the modified example of the sensor element.

A modified example of the sensor element 40 will be described. FIG. 21 is a sectional view of the modified example of the sensor element. FIG. 22 is a top view of the modified example of the sensor element. The sensor element 40 in the embodiments described above may have a configuration illustrated in FIGS. 21, 22 in place of the configuration depicted in FIGS. 4B, 4C. As illustrated in FIGS. 21 and 22, the modified example of the sensor element 40 depicted therein is that the film-shaped sensors 45 bonded to the mount film 41 are covered by cover films 91 for moisture-proof. The cover film 91 covering the film-shaped sensor 45 is configured by stacking an adhesive sheet 92, a base sheet 93 and a desiccant sheet 94 sequentially from under. The adhesive sheet 92 of the cover film 91 is bonded onto the upper surface of the film-shaped sensor 45. An outer peripheral edge of the cover film 91 is bonded onto the surface, onto which the film-shaped sensor 45 is bonded, of the mount film 41 in a state of covering the film-shaped sensor 45. The film-shaped sensor 45 is sealed by the cover film 91 and the mount film 41 and is thereby prevented from being exposed to external air. The film-shaped sensor 45 being prevented from being exposed to the external air, a moisture-proof effect is yielded. As depicted in FIG. 22, each film-shaped sensor 45 is covered by one cover film 91. The example in FIG. 22 is that a planar shape of the cover film 91 is rectangular but is not limited to the shape depicted in FIG. 22. It may be sufficient that the planar shape of the cover film 91 is a shape enabling the film-shaped sensor 45 to be covered. A thickness of the cover film 91 ranges from, e.g., 10 μm to 100 μm.

Materials of the base sheet 93 and the desiccant sheet 94 of the cover film 91 are the same as the materials of the base sheet 41a and the desiccant sheet 41b of the mount film 41. A material of the adhesive sheet 92 of the cover film 91 is the same as the material of the adhesive sheet 45a. When the material of the base sheet 93 of the cover film 91 is a film having a tack property, the adhesive sheet 92 of the cover film 91 may not be used. In this case, the base sheet 93 is bonded directly to the film-shaped sensor 45 and the mount film 41. The desiccant sheet 94 may be omitted in the cover film 91.

The cover film 91 is exfoliated from the mount film 41 together with the film-shaped sensor 45 when the film-shaped sensor 45 is peeled off from the mount film 41. The cover film 91 remains in the state of being bonded to the film-shaped sensor 45 when the film-shaped sensor 45 is exfoliated from the mount film 41. Apart of the cover film 91 may be firmly bonded to the mount film 41. In this case, when the film-shaped sensor 45 is peeled off from the mount film 41, the cover film 91 is exfoliated from the film-shaped sensor 45 and collected together with the mount film 41.

One cover film 91 is prepared for one film-shaped sensor 45 in the example given above. However, the single cover film 91 may also be configured to take the same shape as the shape of the mount film 41 and to cover the plurality of film-shaped sensors 45.

What is claimed is:

1. A sensor element comprising:
   a tape-shaped mount film; and
   a plurality of film-shaped sensors bonded on one surface of the mount film,
   wherein the front and rear film-shaped sensors are spaced at a predetermined distance in a lengthwise direction of the mount film, and a crosswise length of each film-shaped sensor is shorter by a predetermined quantity than a crosswise length of the mount film, each film-shaped sensor has side portions that are substantially parallel to the lengthwise direction of the mount film, each side portion having a front side portion and a rear side portion;

each film-shaped sensor includes protruded portions that extend outward from the side portions between the front side portion and the rear side portion such that each protruded portion is closer to an edge of the mount film than the front side portion and the rear side portion, and each film-shaped sensor is configured so that the side portions provided with the protruded portions are bonded substantially in parallel to a longitudinal direction of the mount film at a central portion of the one surface of the mount film.

2. The sensor element according to claim 1, wherein an end portion of the film-shaped sensor is exfoliated from the mount film when bending a portion, under the end portion of a certain film-shaped sensor, of the mount film in a longitudinal direction of the sensor element at a curvature equal to or smaller than a predetermined curvature with a posture of directing inward an undersurface defined as a surface different from the one surface.

3. The sensor element according to claim 1, wherein the mount film has a hygroscopic property.

4. The sensor element according to claim 1, further comprising a cover film bonded to the one surface of the mount film in a state of covering the film-shaped sensor.

5. The sensor element according to claim 1, wherein the cover film has a hygroscopic property.

6. A sensor cartridge comprising:
a reel wound with the sensor element according to claim 1;
a case to house the reel therein, the case including a sensor protruding port to admit passage of the sensor element wound on the reel and a film housing port to admit passage of the mount film for the sensor element, the sensor protruding port receiving insertion of the sensor element unwound from the reel with a posture of directing an undersurface of the mount film toward the film housing port; and
a rotary body to be housed in the case and enabled to rotate from outside the case, the rotary body driving the sensor element in an unwinding direction of the sensor element wound on the reel, the sensor element being inserted into the sensor protruding portion with the posture of directing the undersurface of the mount film toward the film housing port and returning to within the case via the film housing port after the film-shaped sensor has been removed at a portion in the vicinity of the sensor protruding port,
wherein a portion of the case, existing between the sensor protruding port and the film housing port, has such a shape that at least a part of the mount film is bent at a curvature equal to or smaller than the predetermined curvature when bending the mount film along the portion of the case.

7. The sensor cartridge according to claim 6, wherein the sensor element is wound on the reel with a posture of directing inward the one surface of the mount film.

8. A method for manufacturing a sensor element, comprising:
a step of forming a sensor element by bonding a continuous stacked body including a plurality of film-shaped sensors with a bonding layer being interposed between the film-shaped sensor and the sensor element; and
a step of half-cutting a boundary portion of each film-shaped sensor of the sensor element up to at least the bonding layer from the side of the stacked body, wherein
each film-shaped sensor has substantially parallel side portions including a front side portion and a rear side portion; and
each film-shaped sensor includes protruded portions that extend outward from the side portions between the front side portion and the rear side portion.

9. The method for manufacturing the sensor element according to claim 8, wherein the half-cutting step includes half-cutting the mount film from the side of the stacked body at the boundary portion of each film-shaped sensor of the sensor element.

* * * * *